United States Patent
Ito et al.

(10) Patent No.: US 12,209,134 B2
(45) Date of Patent: Jan. 28, 2025

(54) ANTI-HUMAN FN14 ANTIBODY

(71) Applicant: Astellas Pharma Inc., Tokyo (JP)

(72) Inventors: Misato Ito, Tokyo (JP); Risa Kashiwagi, Tokyo (JP); Masakatsu Kawakami, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 826 days.

(21) Appl. No.: 17/290,180

(22) PCT Filed: Oct. 30, 2019

(86) PCT No.: PCT/JP2019/042587
§ 371 (c)(1),
(2) Date: Apr. 29, 2021

(87) PCT Pub. No.: WO2020/090892
PCT Pub. Date: May 7, 2020

(65) Prior Publication Data
US 2021/0388096 A1  Dec. 16, 2021

(30) Foreign Application Priority Data
Oct. 31, 2018 (JP) ................................. 2018-205995

(51) Int. Cl.
*C07K 16/28* (2006.01)
*A61P 35/00* (2006.01)

(52) U.S. Cl.
CPC .......... *C07K 16/2878* (2013.01); *A61P 35/00* (2018.01); *C07K 2317/56* (2013.01); *C07K 2317/76* (2013.01)

(58) Field of Classification Search
CPC ............ C07K 16/2878; C07K 2317/56; C07K 2317/76; A61P 35/00
See application file for complete search history.

(56) References Cited

U.S. PATENT DOCUMENTS

| | | | |
|---|---|---|---|
| 8,609,818 B2 | 12/2013 | Leppard et al. | |
| 8,664,367 B2 | 3/2014 | Wu et al. | |
| 8,841,417 B2 | 9/2014 | Wu et al. | |
| 9,006,397 B2 | 4/2015 | Hoogenraad et al. | |
| 9,303,085 B2 | 4/2016 | Wu et al. | |
| 9,346,888 B2 | 5/2016 | Leppard et al. | |
| 9,409,986 B2 | 8/2016 | Wu et al. | |
| 9,441,038 B2 | 9/2016 | Wu et al. | |
| 9,447,183 B2 | 9/2016 | Wu et al. | |
| 9,447,184 B2 | 9/2016 | Wu et al. | |
| 10,287,359 B2 | 5/2019 | Hoogenraad et al. | |
| 2009/0324602 A1 | 12/2009 | Garber et al. | |
| 2011/0280800 A1 | 11/2011 | Wu et al. | |
| 2012/0258121 A1 | 10/2012 | Leppard et al. | |
| 2013/0195754 A1 | 8/2013 | Wu et al. | |
| 2013/0273036 A1 | 10/2013 | Hoogenraad et al. | |
| 2014/0066385 A1 | 3/2014 | Arai et al. | |
| 2014/0099671 A1 | 4/2014 | Wu et al. | |
| 2014/0178385 A1 | 6/2014 | Leppard et al. | |
| 2014/0205562 A1 | 7/2014 | Wu et al. | |
| 2014/0212379 A1 | 7/2014 | Wu et al. | |
| 2014/0212925 A1 | 7/2014 | Wu et al. | |
| 2014/0220020 A1 | 8/2014 | Wu et al. | |
| 2015/0218278 A1 | 8/2015 | Hoogenraad et al. | |
| 2016/0237160 A1 | 8/2016 | Votsmeier et al. | |
| 2017/0029519 A1 | 2/2017 | Hoogenraad et al. | |
| 2017/0058027 A1 | 3/2017 | Wu et al. | |
| 2018/0057599 A1 | 3/2018 | Hoogenraad et al. | |
| 2019/0389945 A1 | 12/2019 | Wu et al. | |
| 2020/0002430 A1 | 1/2020 | Hoogenraad et al. | |
| 2020/0239586 A1 | 7/2020 | Hoogenraad et al. | |
| 2021/0388096 A1* | 12/2021 | Ito ..................... | A61K 39/3955 |

FOREIGN PATENT DOCUMENTS

| | | |
|---|---|---|
| CO | 6680666 A2 | 5/2013 |
| CO | 6880666 A2 | 5/2013 |
| CO | 6880061 A2 | 6/2014 |
| JP | 2011-523414 A | 8/2011 |
| JP | 2014-510079 A | 4/2014 |
| JP | 2014-529597 A | 11/2014 |
| JP | 2016-521715 A | 7/2016 |
| RU | 2615173 C2 | 4/2017 |
| WO | WO-01/45730 A2 | 6/2001 |
| WO | WO-2006/096487 A2 | 9/2006 |
| WO | WO-2009/020933 A2 | 2/2009 |
| WO | WO-2009/140177 A2 | 11/2009 |
| WO | WO-2012/045671 A1 | 4/2012 |

(Continued)

OTHER PUBLICATIONS

Walsh et al., Post-translational modifications in the context of therapeutic proteins, Nature Biotech., vol. 24, 1241-1252, Publication Date: Oct. 10, 2006 (Year: 2006).*
McSherry et al., Cysteinylation of a monoclonal antibody leads to its inactivation, MABS, vol. 8, No. 4, 718-725; Publication Date: Apr. 6, 2016 (Year: 2016).*
Gura, T., Systems for Identifying New Drugs Are Often Faulty, Science, 1997, 278:1041-1042 (Year: 1997).*

(Continued)

*Primary Examiner* — Peter J Reddig
*Assistant Examiner* — Cheng Lu
(74) *Attorney, Agent, or Firm* — Foley & Lardner LLP

(57) ABSTRACT

Provided is an anti-human Fn14 antibody which binds to human Fn14 to inhibit an action via the human Fn14, thereby preventing or treating cancer cachexia.

The inventors have conducted studies on an anti-human Fn14 antibody, and provided an anti-human Fn14 antibody comprising a heavy chain consisting of the amino acid sequence of SEQ ID NO: 2 and a light chain consisting of the amino acid sequence of SEQ ID NO: 4.

25 Claims, 5 Drawing Sheets
Specification includes a Sequence Listing.

(56) References Cited

FOREIGN PATENT DOCUMENTS

| WO | WO-2012/122513 A2 | 9/2012 |
|----|-------------------|--------|
| WO | WO-2013/018829 A1 | 2/2013 |
| WO | WO-2013/026099 A1 | 2/2013 |
| WO | WO-2014/198817 A1 | 12/2014 |

OTHER PUBLICATIONS

Kaiser, J., First pass at cancer genoome reveals complex landscape, Science, 2006, 313:1370 (Year: 2006).*
Gerdes et al. Emerging understanding of multiscale tumor heterogeneity, Front. Oncol. Dec. 18, 2014 doi: 10.3389/fonc.2014.00366, pp. 1-12 (Year: 2014).*
Office Action dated Jul. 28, 2023 in CN 201980071220.4, with English translation.
Office Action dated Aug. 18, 2023 in CO NC2021/0005769, with English translation.
Office Action dated Sep. 4, 2023 in IL 282650.
Office Action dated Sep. 8, 2023 in TW 108139361, with English translation.
Baracos et al., "Cancer-associated cachexia," Nature Reviews, Jan. 18, 2018, 4:17105, 18 pages.
Choi et al., "Modeling Hepatocellular Toxicity of Enavatuzumab, a Humanized Anti-TweakR Antibody," American Journal of Pharmacology and Toxicology, 2017, 12(2):18-38.
Culp et al., "Antibodies to TWEAK Receptor Inhibit Human Tumor Growth through Dual Mechanisms," Clinical Cancer Research, Jan. 12, 2010, 16(2):497-508.
Evans et al., "Cachexia: A new definition," Clinical Nutrition, 2008, 27:793-799.
Hu et al., "TWEAK/Fnl4 signaling in tumors," Tumor Biology, Jun. 2017, 1-9.
International Search Report dated Jan. 28, 2020 in PCT/JP2019/042587, with English translation.
Johnston et al., "Targeting of Fn14 Prevents Cancer-Induced Cachexia and Prolongs Survival," Cell, 2015, 162:1365-1378.
Lam et al., "Phase I Study of Anavatuzumab, a First-in-Class Humanized Monoclonal Antibody Targeting the TWEAK Receptor, in Patients with Advanced Solid Tumors," Molecular Cancer Therapeutics, Oct. 20, 2017, Mol. Cancer Ther., Jan. 2018 (online Oct. 20, 2017), 17(1):215-221.
Salzmann et al., "Fibroblast Growth Factor Inducible (FN14)-specific Antibodies Concomitantly Display Signaling Pathway-specific Agonistic and Antagonistic Activity," J. Biol. Chem., May 10, 2013, 288(19):13455-13466.
Winkles et al., "The TWEAK-Fn14 cytokine-receptor axis: discovery, biology and therapeutic targeting," Nat. Rev. Drug Discov., May 2008, 7(5):411-425.
Written Opinion dated Jan. 28, 2020 in PCT/JP2019/042587.
Office Action mailed Nov. 22, 2021 in GCC2019-38569.
Office Action dated Jan. 10, 2024 in CA 3,117,930.
Office Action dated Jan. 25, 2022, in RU 2021112416, with English translation.
Office Action dated Nov. 25, 2022 in SG 11202104463Y, with English translation.
Ballyuzek et al., "Cachexia syndrome: The present state of the problem and importance in clinical practice," Terapevtischeskii Arkhiv., 2015, 87(8):113-118, with English abstract.
Mariuzza et al., Ann. Rev. Biophys. Chem., 1987, 16:139-159.
Office Action dated Jun. 24, 2022 in RU 2021112416, with English translation.
Supplementary European Search Report dated Jul. 13, 2022 in EP 198805366.8.
Office Action dated Aug. 18, 2023 in CO NC2021/0005768, with English translation.
Office Action issued Aug. 21, 2024 in In P/93-2021-P-JO, with English translation.
Office Action dated Apr. 29, 2024 in Malaysian Application No. PI2021002365.
Office Action dated Nov. 1, 2024 in UA 202102277, with English translation.

\* cited by examiner

SEQUENCE LISTING

<160> NUMBER OF SEQ ID NOS: 9

<210> SEQ ID NO 1
<211> LENGTH: 1365
<212> TYPE: DNA
<213> ORGANISM: Artificial Sequence
<220> FEATURE:
<223> OTHER INFORMATION: H-chain of 4-1h antibody
<220> FEATURE:
<221> NAME/KEY: CDS
<222> LOCATION: (1)..(1365)

<400> SEQUENCE: 1

```
cag gtg cag cta cag cag tgg ggc gca gga ctg ttg aag cct tcg gag        48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac        96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att       144
Tyr Trp Ser Trp Ile Arg Gln Pro Pro Gly Lys Gly Leu Glu Trp Ile
        35                  40                  45 ggg gaa atc aat cat cgt gga agc acc aac tcc aac ccg tcc ctc aag       192
Gly Glu Ile Asn His Arg Gly Ser Thr Asn Ser Asn Pro Ser Leu Lys
    50                  55                  60 agt cga gac acc ata tca gta gac acg tcc aag aac cag ttc tcc ctg       240
Ser Arg Asp Thr Ile Ser Val Asp Thr Ser Lys Asn Gln Phe Ser Leu
65                  70                  75                  80 agg ctg agg tct gtg acc gcc gcg gac acg gct gtg tat tac tgt gcg       288
Arg Leu Arg Ser Val Thr Ala Ala Asp Thr Ala Val Tyr Tyr Cys Ala
                85                  90                  95 cgc gag ggt ata agt gga agt atg ggg atc tac gac tac agc gga atg       336
Arg Glu Gly Ile Ser Gly Ser Met Gly Ile Tyr Asp Tyr Ser Gly Met
            100                 105                 110 gac gtc tgg ggc caa ggg acc acg gtc acc gtc tcc tca gcc tcc acc       384
Asp Val Trp Gly Gln Gly Thr Thr Val Thr Val Ser Ser Ala Ser Thr
        115                 120                 125 aag ggc cca tcg gtc ttc ccc ctg gca ccc tcc tcc aag agc acc tct       432
Lys Gly Pro Ser Val Phe Pro Leu Ala Pro Ser Ser Lys Ser Thr Ser
    130                 135                 140 ggg ggc aca gcg gcc ctg ggc tgc ctg gtc aag gac tac ttc ccc gaa       480
Gly Gly Thr Ala Ala Leu Gly Cys Leu Val Lys Asp Tyr Phe Pro Glu
145                 150                 155                 160 ccg gtg acg gtg tcg tgg aac tca ggc gcc ctg acc agc ggc gtg cac       528
Pro Val Thr Val Ser Trp Asn Ser Gly Ala Leu Thr Ser Gly Val His
                165                 170                 175 acc ttc ccg gct gtc cta cag tcc tca gga ctc tac tcc ctt agt agc       576
Thr Phe Pro Ala Val Leu Gln Ser Ser Gly Leu Tyr Ser Leu Ser Ser
            180                 185                 190 gtg gtg acc gtg ccc tcc agc agc ttg ggc acc cag acc tac atc tgc       624
Val Val Thr Val Pro Ser Ser Ser Leu Gly Thr Gln Thr Tyr Ile Cys
        195                 200                 205 aac gtg aat cac aag ccc agc aac acc aag gtg gac aag aaa gtt gag       672
Asn Val Asn His Lys Pro Ser Asn Thr Lys Val Asp Lys Lys Val Glu
    210                 215                 220 ccc aaa tct tgt gac aaa act cac aca tgc cca ccg tgc cca gca cct       720
Pro Lys Ser Cys Asp Lys Thr His Thr Cys Pro Pro Cys Pro Ala Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 225 |     |     |     |     | 230 |     |     |     |     | 235 |     |     |      |     |     |     | 240 |

```
gaa gcc gct ggg gga ccg tca gtc ttc ctc ttc ccc cca aaa ccc aag    768
Glu Ala Ala Gly Gly Pro Ser Val Phe Leu Phe Pro Pro Lys Pro Lys
                245                 250                 255 gac acc ctc atg atc tcc cgg acc cct gag gtc aca tgc gtg gtg gtg    816
Asp Thr Leu Met Ile Ser Arg Thr Pro Glu Val Thr Cys Val Val Val
            260                 265                 270 gac gtg agc cac gaa gac cct gag gtc aag ttc aac tgg tac gtg gac    864
Asp Val Ser His Glu Asp Pro Glu Val Lys Phe Asn Trp Tyr Val Asp
        275                 280                 285 ggc gtg gag gtg cat aat gcc aag aca aag ccg cgg gag gag cag tac    912
Gly Val Glu Val His Asn Ala Lys Thr Lys Pro Arg Glu Glu Gln Tyr
    290                 295                 300 aac agc acg tac cgt gtg gtc agc gtc ctc acc gtc ctg cac cag gac    960
Asn Ser Thr Tyr Arg Val Val Ser Val Leu Thr Val Leu His Gln Asp
305                 310                 315                 320 tgg ctg aat ggc aag gag tac aag tgc aag gtc tcc aac aaa gcc ctc   1008
Trp Leu Asn Gly Lys Glu Tyr Lys Cys Lys Val Ser Asn Lys Ala Leu
                325                 330                 335 cca gcc ccc atc gag aaa acc atc tcc aaa gcc aaa ggg cag ccc cga   1056
Pro Ala Pro Ile Glu Lys Thr Ile Ser Lys Ala Lys Gly Gln Pro Arg
            340                 345                 350 gaa cca cag gtg tac acc ctg ccc cca tcc cgg gat gag ctg acc aag   1104
Glu Pro Gln Val Tyr Thr Leu Pro Pro Ser Arg Asp Glu Leu Thr Lys
        355                 360                 365 aac cag gtc agc ctg acc tgc ctg gtc aaa ggc ttc tat ccc agc gac   1152
Asn Gln Val Ser Leu Thr Cys Leu Val Lys Gly Phe Tyr Pro Ser Asp
    370                 375                 380 atc gcc gtg gag tgg gag agc aat ggg cag ccg gag aac aac tac aag   1200
Ile Ala Val Glu Trp Glu Ser Asn Gly Gln Pro Glu Asn Asn Tyr Lys
385                 390                 395                 400 acc acg cct ccc gtg ctg gac tcc gac ggc tcc ttc ttc ctc tac agc   1248
Thr Thr Pro Pro Val Leu Asp Ser Asp Gly Ser Phe Phe Leu Tyr Ser
                405                 410                 415 aag ctc acc gtg gac aag agc agg tgg cag cag ggg aac gtc ttc tca   1296
Lys Leu Thr Val Asp Lys Ser Arg Trp Gln Gln Gly Asn Val Phe Ser
            420                 425                 430 tgc tcc gtg atg cat gag gct ctg cac aac cac tac acg cag aag agc   1344
Cys Ser Val Met His Glu Ala Leu His Asn His Tyr Thr Gln Lys Ser
        435                 440                 445 ctc tcc ctg tct ccg ggt aaa                                       1365
Leu Ser Leu Ser Pro Gly Lys
    450                 455
```

<210> SEQ ID NO 2
<211> LENGTH: 455
<212> TYPE: PRT
<213> ORGANISM: Artificial Sequence
<220> FEATURE:
<223> OTHER INFORMATION: Synthetic Construct

<400> SEQUENCE: 2

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60
```

```
Ser Arg Asp Thr Ile Ser Val Asp Thr Ser Lys Asn Gln Phe Ser Leu
 65                  70                  75                  80

Arg Leu Arg Ser Val Thr Ala Ala Asp Thr Ala Val Tyr Tyr Cys Ala
                 85                  90                  95

Arg Glu Gly Ile Ser Gly Ser Met Gly Ile Tyr Asp Tyr Ser Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 3
<211> LENGTH: 660
```

<212> TYPE: DNA
<213> ORGANISM: Artificial Sequence
<220> FEATURE:
<223> OTHER INFORMATION: L-chain of 4-1h antibody
<220> FEATURE:
<221> NAME/KEY: CDS
<222> LOCATION: (1)..(660)

<400> SEQUENCE: 3

```
gac atc gtg atg acc cag tct cca gac tcc ctg gct gtg tct ctg ggc      48
Asp Ile Val Met Thr Gln Ser Pro Asp Ser Leu Ala Val Ser Leu Gly
1               5                   10                  15 gag agg gcc acc atc aac tgc aag tcc agg cag agt att tta tat agt      96
Glu Arg Ala Thr Ile Asn Cys Lys Ser Arg Gln Ser Ile Leu Tyr Ser
            20                  25                  30 tcc aac aat aag aac tac tta act tgg tac cag cag aaa cca gga cag     144
Ser Asn Asn Lys Asn Tyr Leu Thr Trp Tyr Gln Gln Lys Pro Gly Gln
        35                  40                  45 cct cct aag ttg ctc att tac tgg gca tct acc cgg gaa tcc ggg gtc     192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat agt act cct tac act ttt ggc cag ggg acc aag ctg gag atc     336
Tyr Tyr Ser Thr Pro Tyr Thr Phe Gly Gln Gly Thr Lys Leu Glu Ile
            100                 105                 110 aaa cgg act gtg gct gca cca tct gtc ttc atc ttc ccg cca tct gat     384
Lys Arg Thr Val Ala Ala Pro Ser Val Phe Ile Phe Pro Pro Ser Asp
        115                 120                 125 gag cag ttg aaa tct gga act gcc tct gtt gtg tgc ctg ctg aat aac     432
Glu Gln Leu Lys Ser Gly Thr Ala Ser Val Val Cys Leu Leu Asn Asn
    130                 135                 140 ttc tat ccc aga gag gcc aaa gta cag tgg aag gtg gat aac gcc ctc     480
Phe Tyr Pro Arg Glu Ala Lys Val Gln Trp Lys Val Asp Asn Ala Leu
145                 150                 155                 160 caa tcg ggt aac tcc cag gag agt gtc aca gag cag gac agc aag gac     528
Gln Ser Gly Asn Ser Gln Glu Ser Val Thr Glu Gln Asp Ser Lys Asp
                165                 170                 175 agc acc tac agc ctc agc agc acc ctg acg ctg agc aaa gca gac tac     576
Ser Thr Tyr Ser Leu Ser Ser Thr Leu Thr Leu Ser Lys Ala Asp Tyr
            180                 185                 190 gag aaa cac aaa gtc tac gcc tgc gaa gtc acc cat cag ggc ctg agc     624
Glu Lys His Lys Val Tyr Ala Cys Glu Val Thr His Gln Gly Leu Ser
        195                 200                 205 tcg ccc gtc aca aag agc ttc aac agg gga gag tgt                     660
Ser Pro Val Thr Lys Ser Phe Asn Arg Gly Glu Cys
    210                 215                 220
```

<210> SEQ ID NO 4
<211> LENGTH: 220
<212> TYPE: PRT
<213> ORGANISM: Artificial Sequence
<220> FEATURE:
<223> OTHER INFORMATION: Synthetic Construct

<400> SEQUENCE: 4

```
Asp Ile Val Met Thr Gln Ser Pro Asp Ser Leu Ala Val Ser Leu Gly
1               5                   10                  15
```

-continued

```
Glu Arg Ala Thr Ile Asn Cys Lys Ser Arg Gln Ser Ile Leu Tyr Ser
                 20                  25                  30

Ser Asn Asn Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 5
<211> LENGTH: 1368
<212> TYPE: DNA
<213> ORGANISM: Artificial Sequence
<220> FEATURE:
<223> OTHER INFORMATION: H-chain of 4-1m antibody
<220> FEATURE:
<221> NAME/KEY: CDS
<222> LOCATION: (1)..(1368)

<400> SEQUENCE: 5 gat gtt cag ctg caa gag tct ggc cct ggc ctg gtc aag cct tct cag      48
Asp Val Gln Leu Gln Glu Ser Gly Pro Gly Leu Val Lys Pro Ser Gln
 1               5                  10                  15 tct ctg tct ctg acc tgc gct gtg tac ggc ggc tct ttc tct ggc tac      96
Ser Leu Ser Leu Thr Cys Ala Val Tyr Gly Gly Ser Phe Ser Gly Tyr
                 20                  25                  30 tac tgg tcc tgg atc cgg cag ttc cct ggc aac aag ctg gaa tgg atg     144
Tyr Trp Ser Trp Ile Arg Gln Phe Pro Gly Asn Lys Leu Glu Trp Met
             35                  40                  45 ggc gag atc aac cac cgg ggc tcc acc aac tct aac ccc agc ctg aag     192
Gly Glu Ile Asn His Arg Gly Ser Thr Asn Ser Asn Pro Ser Leu Lys
 50                  55                  60 tcc cgg atc tcc atc acc gtg gac acc tcc aag aac cag ttc ttt ctg     240
Ser Arg Ile Ser Ile Thr Val Asp Thr Ser Lys Asn Gln Phe Phe Leu
 65                  70                  75                  80 cag ctc aac tcc gtg aca acc gag gac acc gcc acc tac tac tgt gcc     288
Gln Leu Asn Ser Val Thr Thr Glu Asp Thr Ala Thr Tyr Tyr Cys Ala
                 85                  90                  95 aga gag ggc atc tct ggc tcc atg ggc atc tac gac tac tcc ggc atg     336
Arg Glu Gly Ile Ser Gly Ser Met Gly Ile Tyr Asp Tyr Ser Gly Met
                100                 105                 110
```

| | | |
|---|---|---|
| gat gtg tgg ggc cag ggc aca ctg gtt acc gtg tct gcc gct aag acc<br>Asp Val Trp Gly Gln Gly Thr Leu Val Thr Val Ser Ala Ala Lys Thr<br>115                    120                    125 | | 384 |
| acc gct cct tcc gtg tat cct ctg gca cct gtg tgt ggc gac acc acc<br>Thr Ala Pro Ser Val Tyr Pro Leu Ala Pro Val Cys Gly Asp Thr Thr<br>130                    135                    140 | | 432 |
| gga agt tct gtg acc ctg gga tgt ctg gtc aag ggc tac ttc ccc gag<br>Gly Ser Ser Val Thr Leu Gly Cys Leu Val Lys Gly Tyr Phe Pro Glu<br>145                    150                    155                    160 | | 480 |
| cct gtg aca ctg acc tgg aac tct ggc tct ctg tcc tct ggc gtg cac<br>Pro Val Thr Leu Thr Trp Asn Ser Gly Ser Leu Ser Ser Gly Val His<br>                    165                    170                    175 | | 528 |
| acc ttt cca gcc gtg ctg cag tct gac ctg tac acc ctg tct agc tcc<br>Thr Phe Pro Ala Val Leu Gln Ser Asp Leu Tyr Thr Leu Ser Ser Ser<br>                  180                    185                    190 | | 576 |
| gtg acc gtg acc tcc tct acc tgg cct agc cag tcc atc acc tgt aac<br>Val Thr Val Thr Ser Ser Thr Trp Pro Ser Gln Ser Ile Thr Cys Asn<br>                    195                    200                    205 | | 624 |
| gtg gcc cat cct gcc tcc agc acc aag gtg gac aag aag atc gag cct<br>Val Ala His Pro Ala Ser Ser Thr Lys Val Asp Lys Lys Ile Glu Pro<br>210                    215                    220 | | 672 |
| cgg ggc cct acc atc aag cct tgt cct cca tgc aag tgc ccc gct cct<br>Arg Gly Pro Thr Ile Lys Pro Cys Pro Pro Cys Lys Cys Pro Ala Pro<br>225                    230                    235                    240 | | 720 |
| aat ctg ctc gga ggc ccc tcc gtg ttc atc ttc cca cct aag atc aag<br>Asn Leu Leu Gly Gly Pro Ser Val Phe Ile Phe Pro Pro Lys Ile Lys<br>                    245                    250                    255 | | 768 |
| gac gtg ctg atg atc tcc ctg tct cct atc gtg acc tgc gtg gtg gtg<br>Asp Val Leu Met Ile Ser Leu Ser Pro Ile Val Thr Cys Val Val Val<br>                  260                    265                    270 | | 816 |
| gcc gtg tcc gag gat gat cct gac gtg cag atc agt tgg ttc gtg aac<br>Ala Val Ser Glu Asp Asp Pro Asp Val Gln Ile Ser Trp Phe Val Asn<br>275                    280                    285 | | 864 |
| aac gtg gaa gtg cac acc gct cag acc cag aca cac aga gag gac tac<br>Asn Val Glu Val His Thr Ala Gln Thr Gln Thr His Arg Glu Asp Tyr<br>              290                    295                    300 | | 912 |
| aac agc acc ctg aga gtg gtg tct gcc ctg cct atc cag cat cag gat<br>Asn Ser Thr Leu Arg Val Val Ser Ala Leu Pro Ile Gln His Gln Asp<br>305                    310                    315                    320 | | 960 |
| tgg atg tcc ggc aaa gag ttc aag tgc aaa gtg aac aac aag gac ctg<br>Trp Met Ser Gly Lys Glu Phe Lys Cys Lys Val Asn Asn Lys Asp Leu<br>                    325                    330                    335 | | 1008 |
| cct gct cca atc gag cgg acc atc tct aag cct aag ggc tct gtc agg<br>Pro Ala Pro Ile Glu Arg Thr Ile Ser Lys Pro Lys Gly Ser Val Arg<br>                  340                    345                    350 | | 1056 |
| gcc cct cag gtg tac gtt ttg cct cca cct gag gaa gag atg acc aag<br>Ala Pro Gln Val Tyr Val Leu Pro Pro Pro Glu Glu Glu Met Thr Lys<br>              355                    360                    365 | | 1104 |
| aaa caa gtg acc ctg aca tgc atg gtc acc gac ttc atg ccc gag gac<br>Lys Gln Val Thr Leu Thr Cys Met Val Thr Asp Phe Met Pro Glu Asp<br>370                    375                    380 | | 1152 |
| atc tac gtg gaa tgg acc aac aac ggc aag acc gag ctg aac tac aag<br>Ile Tyr Val Glu Trp Thr Asn Asn Gly Lys Thr Glu Leu Asn Tyr Lys<br>385                    390                    395                    400 | | 1200 |
| aac acc gag cca gtg ctg gac tcc gac ggc tcc tac ttc atg tac tcc<br>Asn Thr Glu Pro Val Leu Asp Ser Asp Gly Ser Tyr Phe Met Tyr Ser<br>                    405                    410                    415 | | 1248 |
| aag ctg cgc gtc gag aag aag aac tgg gtc gag aga aac tcc tac tcc<br>Lys Leu Arg Val Glu Lys Lys Asn Trp Val Glu Arg Asn Ser Tyr Ser | | 1296 |

```
                    420                 425                 430
tgc tcc gtg gtg cac gag ggc ctg cac aat cac cac acc acc aag tcc    1344
Cys Ser Val Val His Glu Gly Leu His Asn His His Thr Thr Lys Ser
        435                 440                 445 ttc tct cgg acc cct ggc aag tga                                    1368
Phe Ser Arg Thr Pro Gly Lys
    450                 455

<210> SEQ ID NO 6
<211> LENGTH: 455
<212> TYPE: PRT
<213> ORGANISM: Artificial Sequence
<220> FEATURE:
<223> OTHER INFORMATION: Synthetic Construct

<400> SEQUENCE: 6

Asp Val Gln Leu Gln Glu Ser Gly Pro Gly Leu Val Lys Pro Ser Gln
1               5                   10                  15

Ser Leu Ser Leu Thr Cys Ala Val Tyr Gly Gly Ser Phe Ser Gly Tyr
            20                  25                  30

Tyr Trp Ser Trp Ile Arg Gln Phe Pro Gly Asn Lys Leu Glu Trp Met
        35                  40                  45

Gly Glu Ile Asn His Arg Gly Ser Thr Asn Ser Asn Pro Ser Leu Lys
    50                  55                  60

Ser Arg Ile Ser Ile Thr Val Asp Thr Ser Lys Asn Gln Phe Phe Leu
65                  70                  75                  80

Gln Leu Asn Ser Val Thr Thr Glu Asp Thr Ala Thr Tyr Tyr Cys Ala
            85                  90                  95

Arg Glu Gly Ile Ser Gly Ser Met Gly Ile Tyr Asp Tyr Ser Gly Met
            100                 105                 110

Asp Val Trp Gly Gln Gly Thr Leu Val Thr Val Ser Ala Ala Lys Thr
        115                 120                 125

Thr Ala Pro Ser Val Tyr Pro Leu Ala Pro Val Cys Gly Asp Thr Thr
    130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
            165                 170                 175

Thr Phe Pro Ala Val Leu Gln Ser Asp Leu Tyr Thr Leu Ser Ser Ser
        180                 185                 190

Val Thr Val Thr Ser Ser Thr Trp Pro Ser Gln Ser Ile Thr Cys Asn
    195                 200                 205

Val Ala His Pro Ala Ser Ser Thr Lys Val Asp Lys Lys Ile Glu Pro
    210                 215                 220

Arg Gly Pro Thr Ile Lys Pro Cys Pro Pro Cys Lys Cys Pro Ala Pro
225                 230                 235                 240

Asn Leu Leu Gly Gly Pro Ser Val Phe Ile Phe Pro Pro Lys Ile Lys
            245                 250                 255

Asp Val Leu Met Ile Ser Leu Ser Pro Ile Val Thr Cys Val Val Val
        260                 265                 270

Ala Val Ser Glu Asp Asp Pro Asp Val Gln Ile Ser Trp Phe Val Asn
    275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320
```

```
Trp Met Ser Gly Lys Glu Phe Lys Cys Lys Val Asn Asn Lys Asp Leu
                325                 330                 335

Pro Ala Pro Ile Glu Arg Thr Ile Ser Lys Pro Lys Gly Ser Val Arg
            340                 345                 350

Ala Pro Gln Val Tyr Val Leu Pro Pro Glu Glu Met Thr Lys
        355                 360                 365

Lys Gln Val Thr Leu Thr Cys Met Val Thr Asp Phe Met Pro Glu Asp
    370                 375                 380

Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
                405                 410                 415

Lys Leu Arg Val Glu Lys Lys Asn Trp Val Glu Arg Asn Ser Tyr Ser
            420                 425                 430

Cys Ser Val Val His Glu Gly Leu His Asn His His Thr Thr Lys Ser
        435                 440                 445

Phe Ser Arg Thr Pro Gly Lys
    450                 455

<210> SEQ ID NO 7
<211> LENGTH: 663
<212> TYPE: DNA
<213> ORGANISM: Artificial Sequence
<220> FEATURE:
<223> OTHER INFORMATION: L-chain of 4-1m antibody
<220> FEATURE:
<221> NAME/KEY: CDS
<222> LOCATION: (1)..(663)

<400> SEQUENCE: 7 gac atc gtg atg tct cag agc cct tcc tct ctg gcc gtg tcc gtg gga      48
Asp Ile Val Met Ser Gln Ser Pro Ser Ser Leu Ala Val Ser Val Gly
1               5                   10                  15 gag aaa gtg acc atg tcc tgc aag tcc cgg cag tcc atc ctg tac tcc      96
Glu Lys Val Thr Met Ser Cys Lys Ser Arg Gln Ser Ile Leu Tyr Ser
            20                  25                  30 tcc aac aac aag aac tac ctg acc tgg tat cag cag aag ccc ggc cag     144
Ser Asn Asn Lys Asn Tyr Leu Thr Trp Tyr Gln Gln Lys Pro Gly Gln
        35                  40                  45 tct cct aag ctg ctg atc tac tgg gcc tcc acc aga gaa tct ggc gtg     192
Ser Pro Lys Leu Leu Ile Tyr Trp Ala Ser Thr Arg Glu Ser Gly Val
    50                  55                  60 ccc gat aga ttc acc ggc tct ggc tct ggc acc gac ttt acc ctg acc     240
Pro Asp Arg Phe Thr Gly Ser Gly Ser Gly Thr Asp Phe Thr Leu Thr
65                  70                  75                  80 atc tcc tcc gtg aag gcc gag gat ctg gct gtg tac tac tgc cag cag     288
Ile Ser Ser Val Lys Ala Glu Asp Leu Ala Val Tyr Tyr Cys Gln Gln
                85                  90                  95 tac tac agc acc cct tac acc ttt ggc tcc ggc acc aag ctg gaa atc     336
Tyr Tyr Ser Thr Pro Tyr Thr Phe Gly Ser Gly Thr Lys Leu Glu Ile
            100                 105                 110 aag aga gct gac gcc gct cct acc gtg tct atc ttc cca cct agc tcc     384
Lys Arg Ala Asp Ala Ala Pro Thr Val Ser Ile Phe Pro Pro Ser Ser
        115                 120                 125 gag cag ctg acc tct ggc gga gct tct gtc gtg tgc ttc ctg aac aac     432
Glu Gln Leu Thr Ser Gly Gly Ala Ser Val Val Cys Phe Leu Asn Asn
    130                 135                 140 ttc tac ccc aag gac atc aac gtg aag tgg aag atc gac ggc tcc gag     480
Phe Tyr Pro Lys Asp Ile Asn Val Lys Trp Lys Ile Asp Gly Ser Glu
```

```
                145                 150                 155                 160
aga cag aac ggc gtg ctg aac tct tgg acc gac cag gac tcc aag gac           528
Arg Gln Asn Gly Val Leu Asn Ser Trp Thr Asp Gln Asp Ser Lys Asp
                    165                 170                 175 agc acc tac tcc atg tcc tcc aca ctg acc ctg aca aag gac gag tac           576
Ser Thr Tyr Ser Met Ser Ser Thr Leu Thr Leu Thr Lys Asp Glu Tyr
            180                 185                 190 gag cgg cac aac tcc tat acc tgc gag gct acc cac aag acc tcc acc           624
Glu Arg His Asn Ser Tyr Thr Cys Glu Ala Thr His Lys Thr Ser Thr
            195                 200                 205 tct cca atc gtg aag tcc ttc aac cgg aac gag tgc tga                       663
Ser Pro Ile Val Lys Ser Phe Asn Arg Asn Glu Cys
            210                 215                 220

<210> SEQ ID NO 8
<211> LENGTH: 220
<212> TYPE: PRT
<213> ORGANISM: Artificial Sequence
<220> FEATURE:
<223> OTHER INFORMATION: Synthetic Construct

<400> SEQUENCE: 8

Asp Ile Val Met Ser Gln Ser Pro Ser Ser Leu Ala Val Ser Val Gly
1               5                   10                  15

Glu Lys Val Thr Met Ser Cys Lys Ser Arg Gln Ser Ile Leu Tyr Ser
            20                  25                  30

Ser Asn Asn Lys Asn Tyr Leu Thr Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Thr Pro Tyr Thr Phe Gly Ser Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
            195                 200                 205

Ser Pro Ile Val Lys Ser Phe Asn Arg Asn Glu Cys
            210                 215                 220
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Ile Glu Gly Arg Met Asp Gly Gly Gly
1               5
```

ANTI-HUMAN FN14 ANTIBODY

TECHNICAL FIELD

The present invention relates to an anti-human Fn14 antibody.

BACKGROUND ART

Cachexia is a complex metabolic syndrome associated with underlying illness and characterized by loss of muscle with or without loss of fat mass. The prominent clinical feature of cachexia is weight loss in adults or growth failure in children (Non-Patent Document 1). Approximately 80% of patients with advanced cancers have cachexia, which is called cancer cachexia. Cachexia lowers a prognosis of a patient or a quality of life (QOL) by resistance to treatments, and is related to an increase in the rate of death. However, there are no effective treatments for cachexia. Although the mechanism of the occurrence of cachexia is not clear, cachexia has been perceived as an inflammatory state of the whole body via various cytokines in recent years (Non-Patent Document 2).

Fibroblast growth factor-inducible 14 (Fn14) (also referred to as TNFRSF12A) is a member of tumor necrosis factor receptor family. Fn14 is also known as a Tweak receptor, which binds to a TNF-like weak inducer of apoptosis (Tweak). Tweak-dependent or independent activation of Fn14 is known to activate the NFkB signaling pathway and to control cell proliferation, migration, differentiation, and apoptosis, as well as inflammation involved in angiogenesis, tissue damage, and regeneration (Non-Patent Document 3).

Regarding the relationship with cancers, it has been reported that Fn14 is overexpressed in various solid cancers (Non-Patent Document 4) and that Fn14 is involved in tumor progression and metastasis (Non-Patent Document 5). In addition, it has been reported that in a mouse model of cancer cachexia, an anti-Fn14 antibody is effective in improving the symptoms of cachexia, and the action thereof is due to Fn14 inhibition in the tumor (Non-Patent Document 6).

Meanwhile, the activation of Fn14 may cause the production of an inflammatory cytokine and worsen the inflammatory state. Enavatuzumab (Patent Document 1), that is under clinical development, has been reported as an agonist antibody against human Fn14. Hepatotoxicity has been reported in phase I clinical trial of Enavatuzumab (Non-Patent Document 7), and it has been suggested that inflammation may be caused by Enavatuzumab treatment (Non-Patent Document 8).

A mouse monoclonal antibody CRCBT-06-002 has been reported as an antibody which binds to human Fn14 and has antagonist activity, but does not have agonist activity under specific conditions (Patent Document 2). CRCBT-06-002 has been reported to have antagonist activity that inhibits IL-8 production induced by Tweak stimulation in a human malignant melanoma-derived cell line A375 cell and to have effectiveness in a mouse model of cancer cachexia. However, agonist activity that induces IL-8 production from A375 cells in the absence of Tweak remains (Patent Document 2).

An anti-Fn14 antagonist antibody which has no agonist activity and can avoid undesirable side effects is not known.

RELATED ART

Patent Document

[Patent Document 1] WO 2009/020933
[Patent Document 2] WO 2013/026099

Non-Patent Document

[Non-Patent Document 1] Evans W J et al., Clin Nutr. 2008, Vol. 27, p. 793-799
[Non-Patent Document 2] Baracos V E et al., Nat Rev Dis Primers. 2018, Vol. 4 Article number 17105, p. 1-18
[Non-Patent Document 3] Winkles J A, Nat Rev Drug Discov. 2008, Vol. 7, p. 411-425
[Non-Patent Document 4] Culp P A et al., Clin Cancer Res. 2010, Vol. 16, p. 497-508
[Non-Patent Document 5] HU G et al., Tumor Biol. 2017, Vol. 39 June, p. 1-9
[Non-Patent Document 6] Johnston A J et al., Cell. 2015, Vol. 162, p. 1365-1378
[Non-Patent Document 7] Lam E T et al., Mol Cancer Ther. 2018, Vol. 17, p. 215-221
[Non-Patent Document 8] Choi D et al., Am J Pharmacol Toxicol. 2017, Vol. 12, p. 18-38

DISCLOSURE OF INVENTION

Problems to be Solved by the Invention

An object of the present invention is to provide an anti-human Fn14 antibody having excellent safety that retains high antagonist activity and has reduced agonist activity as compared to conventional antibodies.

Means for Solving the Problems

The inventors have conducted intensive studies on the preparation of an anti-human Fn14 antibody, and as a result, prepared an anti-human Fn14 antibody comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 114 of SEQ ID NO: 2, and a light chain variable region comprising CDR1 consisting of the amino acid sequence of amino acid numbers 24 to 40 of SEQ ID NO: 4, CDR2 consisting of the amino acid sequence of amino acid numbers 56 to 62 of SEQ ID NO: 4, and CDR3 consisting of the amino acid sequence of amino acid numbers 95 to 103 of SEQ ID NO: 4 (Examples 2 to 4). The inventors have found that the antibody binds to human Fn14 (Example 6), inhibits NFkB activation and IL-8 production induced by Tweak stimulation (Examples 7 and 8), and does not induce IL-8 production in the absence of Tweak (Example 8). As a result, an anti-human Fn14 antibody having antagonist activity but not agonist activity was provided, and the present invention was completed. Furthermore, the inventors have found that an antibody in which the above antibody is murinized (Example 4) suppresses a decrease in the weight and muscle mass in a mouse model of cancer cachexia (Example 9), and that the survival period is prolonged in a case where the antibody and gemcitabine are used in combination as compared to administration of the antibody alone or the gemcitabine alone (Example 10).

According to the present invention, for example, the following invention is provided.

[1]

An anti-human Fn14 antibody or an antigen-binding fragment thereof comprising:
- a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 114 of SEQ ID NO: 2; and
- a light chain variable region comprising CDR1 consisting of the amino acid sequence of amino acid numbers 24 to 40 of SEQ ID NO: 4, CDR2 consisting of the amino acid sequence of amino acid numbers 56 to 62 of SEQ ID NO: 4, and CDR3 consisting of the amino acid sequence of amino acid numbers 95 to 103 of SEQ ID NO: 4.

[2]

The anti-human Fn14 antibody or the antigen-binding fragment thereof according to [1], selected from the following (1) and (2):
- (1) an anti-human Fn14 antibody or an antigen-binding fragment thereof comprising a heavy chain variable region consisting of the amino acid sequence of amino acid numbers 1 to 125 of SEQ ID NO: 2 and a light chain variable region consisting of the amino acid sequence of amino acid numbers 1 to 114 of SEQ ID NO: 4; and
- (2) an antibody or an antigen-binding fragment thereof formed by posttranslational modification of the anti-human Fn14 antibody or the antigen-binding fragment thereof of (1).

[3]

The anti-human Fn14 antibody or the antigen-binding fragment thereof according to [2], comprising:
- a heavy chain variable region consisting of the amino acid sequence of amino acid numbers 1 to 125 of SEQ ID NO: 2; and
- a light chain variable region consisting of the amino acid sequence of amino acid numbers 1 to 114 of SEQ ID NO: 4.

[4]

The anti-human Fn14 antibody or the antigen-binding fragment thereof according to [2], wherein the posttranslational modification is pyroglutamylation at the N terminal of the heavy chain variable region and/or deletion of lysine at the C terminal of the heavy chain.

[5]

The anti-human Fn14 antibody or the antigen-binding fragment thereof according to [2], comprising:
- a heavy chain variable region consisting of the amino acid sequence of amino acid numbers 1 to 125 of SEQ ID NO: 2, in which glutamine of amino acid number 1 of SEQ ID NO: 2 is modified to pyroglutamic acid; and
- a light chain variable region consisting of the amino acid sequence of amino acid numbers 1 to 114 of SEQ ID NO: 4.

[6]

The anti-human Fn14 antibody according to [2], selected from the following (3) and (4):
- (3) an anti-human Fn14 antibody comprising a heavy chain consisting of the amino acid sequence represented by SEQ ID NO: 2 and a light chain consisting of the amino acid sequence represented by SEQ ID NO: 4; and
- (4) an anti-human Fn14 antibody formed by posttranslational modification of the antibody of (3).

[7]

The anti-human Fn14 antibody according to [6], comprising:
- a heavy chain consisting of the amino acid sequence represented by SEQ ID NO: 2; and
- a light chain consisting of the amino acid sequence represented by SEQ ID NO: 4

[8]

The anti-human Fn14 antibody according to [6], wherein the posttranslational modification is pyroglutamylation at the N terminal of the heavy chain and/or deletion of lysine at the C terminal of the heavy chain.

[9]

The anti-human Fn14 antibody according to [8], comprising:
- a heavy chain consisting of the amino acid sequence of amino acid numbers 1 to 454 of SEQ ID NO: 2, in which glutamine of amino acid number 1 of SEQ ID NO: 2 is modified to pyroglutamic acid; and
- a light chain consisting of the amino acid sequence represented by SEQ ID NO: 4.

[10]

The antigen-binding fragment according to any one of [1] to [5], which is a single chain variable region fragment, Fab, Fab', or F(ab')$_2$.

[11]

A polynucleotide comprising:
- a base sequence encoding the heavy chain variable region of the anti-human Fn14 antibody or the antigen-binding fragment thereof according to [3].

[12]

A polynucleotide comprising:
- a base sequence encoding the light chain variable region of the anti-human Fn14 antibody or the antigen-binding fragment thereof according to [3].

[13]

An expression vector comprising:
- the polynucleotide according to [11] and/or [12].

[14]

A host cell selected from the group consisting of the following (a) to (d):
- (a) a host cell transformed with an expression vector comprising a polynucleotide comprising a base sequence encoding the heavy chain variable region of the anti-human Fn14 antibody or the antigen-binding fragment thereof according to [3] and a polynucleotide comprising a base sequence encoding the light chain variable region of the antibody or the antigen-binding fragment thereof;
- (b) a host cell transformed with an expression vector comprising a polynucleotide comprising a base sequence encoding the heavy chain variable region of the anti-human Fn14 antibody or the antigen-binding fragment thereof according to [3], and an expression vector comprising a polynucleotide comprising a base sequence encoding the light chain variable region of the antibody or the antigen-binding fragment thereof;
- (c) a host cell transformed with an expression vector comprising a polynucleotide comprising a base sequence encoding the heavy chain variable region of the anti-human Fn14 antibody or the antigen-binding fragment thereof according to [3]; and
- (d) a host cell transformed with an expression vector comprising a polynucleotide comprising a base sequence encoding the light chain variable region of the anti-human Fn14 antibody or the antigen-binding fragment thereof according to [3].

[15]

A host cell selected from the group consisting of the following (e) to (h):
- (e) a host cell transformed with an expression vector comprising a polynucleotide comprising a base sequence encoding the heavy chain of the anti-human Fn14 antibody according to [7] and a polynucleotide comprising a base sequence encoding the light chain of the antibody;
- (f) a host cell transformed with an expression vector comprising a polynucleotide comprising a base sequence encoding the heavy chain of the anti-human Fn14 antibody according to [7], and an expression vector comprising a polynucleotide comprising a base sequence encoding the light chain of the antibody;
- (g) a host cell transformed with an expression vector comprising a polynucleotide comprising a base sequence encoding the heavy chain of the anti-human Fn14 antibody according to [7]; and
- (h) a host cell transformed with an expression vector comprising a polynucleotide comprising a base sequence encoding the light chain of the anti-human Fn14 antibody according to [7].

[16]

A method for producing an anti-human Fn14 antibody or an antigen-binding fragment thereof, the method comprising:
a step of culturing a host cell selected from the group consisting of the following (A) to (C) to express an anti-human Fn14 antibody or an antigen-binding fragment thereof:
- (A) a host cell transformed with an expression vector comprising a polynucleotide comprising a base sequence encoding the heavy chain variable region of the anti-human Fn14 antibody or the antigen-binding fragment thereof according to [3] and a polynucleotide comprising a base sequence encoding the light chain variable region of the antibody or the antigen-binding fragment thereof;
- (B) a host cell transformed with an expression vector comprising a polynucleotide comprising a base sequence encoding the heavy chain variable region of the anti-human Fn14 antibody or the antigen-binding fragment thereof according to [3], and an expression vector comprising a polynucleotide comprising a base sequence encoding the light chain variable region of the antibody or the antigen-binding fragment thereof; and
- (C) a host cell transformed with an expression vector comprising a polynucleotide comprising a base sequence encoding the heavy chain variable region of the anti-human Fn14 antibody or the antigen-binding fragment thereof according to [3], and a host cell transformed with an expression vector comprising a polynucleotide comprising a base sequence encoding the light chain variable region of the antibody or the antigen-binding fragment thereof.

[17]

A method for producing an anti-human Fn14 antibody comprising:
a step of culturing a host cell selected from the group consisting of the following (D) to (F) to express an anti-human Fn14 antibody:
- (D) a host cell transformed with an expression vector comprising a polynucleotide comprising a base sequence encoding the heavy chain of the anti-human Fn14 antibody according to [7] and a polynucleotide comprising a base sequence encoding the light chain of the antibody;
- (E) a host cell transformed with an expression vector comprising a polynucleotide comprising a base sequence encoding the heavy chain of the anti-human Fn14 antibody according to [7], and an expression vector comprising a polynucleotide comprising a base sequence encoding the light chain of the antibody; and
- (F) a host cell transformed with an expression vector comprising a polynucleotide comprising a base sequence encoding the heavy chain of the anti-human Fn14 antibody according to [7], and a host cell transformed with an expression vector comprising a polynucleotide comprising a base sequence encoding the light chain of the anti-human Fn14 antibody.

[18]

An anti-human Fn14 antibody or an antigen-binding fragment thereof produced by the method according to [16].

[19]

An anti-human Fn14 antibody produced by the method according to [17].

[20]

A pharmaceutical composition comprising:
the anti-human Fn14 antibody or the antigen-binding fragment thereof according to any one of [1] to [10], [18], and [19]; and
a pharmaceutically acceptable excipient.

[21]

A pharmaceutical composition comprising:
the anti-human Fn14 antibody or the antigen-binding fragment thereof according to [3];
the anti-human Fn14 antibody or the antigen-binding fragment thereof according to [5]; and
a pharmaceutically acceptable excipient.

[22]

A pharmaceutical composition comprising:
the anti-human Fn14 antibody according to [7];
the anti-human Fn14 antibody according to [9]; and
a pharmaceutically acceptable excipient.

[23]

The pharmaceutical composition according to any one of [20] to [22], which is a pharmaceutical composition for preventing or treating cancer cachexia.

[24]

A method for preventing or treating cancer cachexia, the method comprising:
a step of administering a therapeutically effective amount of the anti-human Fn14 antibody or the antigen-binding fragment thereof according to any one of [1] to [10], [18], and [19].

[25]

The anti-human Fn14 antibody or the antigen-binding fragment thereof according to any one of [1] to [10], [18], and [19], which is for use in preventing or treating cancer cachexia.

[26]

Use of the anti-human Fn14 antibody or the antigen-binding fragment thereof according to any one of [1] to [10], [18], and [19] for the manufacturing of a pharmaceutical composition for preventing or treating cancer cachexia.

[27]

A pharmaceutical composition for preventing or treating cancer or cancer cachexia, comprising:
the anti-human Fn14 antibody or the antigen-binding fragment thereof according to any one of [1] to [10], [18], and [19] as an active ingredient, wherein the pharmaceutical composition is used in combination with an anticancer agent.

[28]

A pharmaceutical composition for preventing or treating cancer or cancer cachexia, comprising:
an anticancer agent,
wherein the pharmaceutical composition is used in combination with the anti-human Fn14 antibody or the antigen-binding fragment thereof according to any one of [1] to [10], [18], and [19].

Effects of the Invention

An anti-human Fn14 antibody of the present invention acts to suppress inflammation by inhibiting the activation of human Fn14 induced by Tweak stimulation without exhibiting agonist activity against human Fn14, and can be used as an agent for preventing or treating cancer cachexia.

EMBODIMENTS FOR CARRYING OUT THE INVENTION

Figure 1:
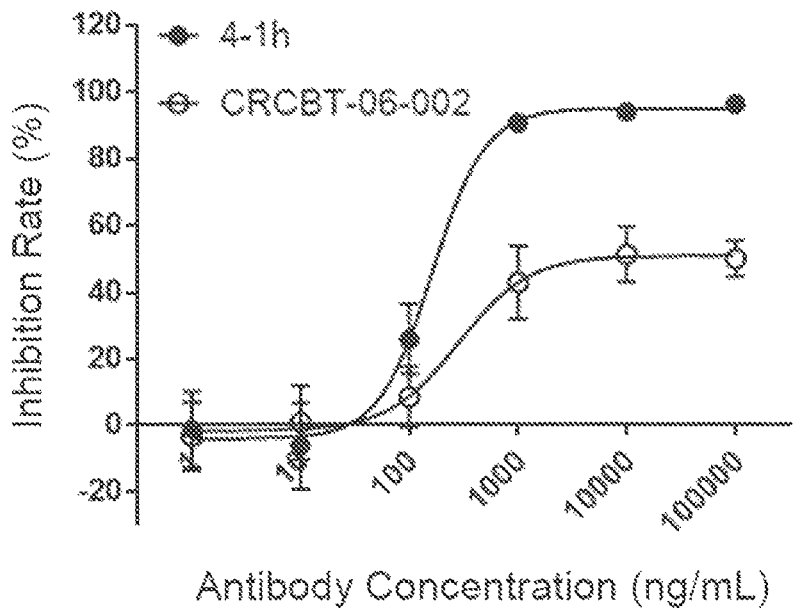
FIG. 1 shows an inhibitory effect of an anti-human Fn14 antibody on inflammatory cytokine IL-8 production induced by Tweak stimulation in A375 cells. The vertical axis represents an inhibition rate (%), and the horizontal axis represents an antibody concentration (ng/mL).

Hereinafter, the present invention will be described in detail.

There are five classes of IgG, IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, Igδ, and Igε corresponding to IgG, IgM, IgA, IgD, and IgE, respectively. Further, four subclasses of IgG1, IgG2, IgG3, and IgG4 are present in IgG, and the heavy chains respectively corresponding thereto are referred to as Igγ1, Igγ2, Igγ3, and Igγ4. Light chain usually consists of a polypeptide chain comprising 220 amino acids, two types of which, type L and type K are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in Igμ and Igε chains) and two of them are present in the light chain; one loop is formed per 100 to 110 amino acid residues, and this steric structure is similar among the loops and are referred to as a structural unit or a domain. The domain located at the N terminal side in both of the heavy chain and the light chain, whose amino acid sequence is not constant even in a case of a sample from the same class (sub class) of the same kind of animal is referred to as a variable region, and respective domains are referred to as a heavy chain variable region (VH) and a light chain variable region (VL). The amino acid sequence of the C terminal side from the variable region is nearly constant in each class or subclass and is referred to as a constant region (respective domains are represented as CH1, CH2, CH3, or CL, respectively).

An antigenic binding site of an antibody is configured of VH and VL, and the binding specificity depends on the amino acid sequence of this site. On the other hand, biological activities such as binding to complements and various Fc receptor expression cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Various antigen-binding fragments comprising VH and VL of an antibody also have antigen-binding activities, and representative examples of such an antigen-binding fragment include a single chain variable region fragment (scFv), Fab, Fab', and F(ab')$_2$. scFv is a monovalent antibody fragment which is configured of VH and VL connected to each other via a linker. Fab is a monovalent antibody fragment which is configured of a light chain and a heavy chain fragment comprising VH, a CH1 domain, and a portion of a hinge region. Fab' is a monovalent antibody fragment which is configured of a light chain and a heavy chain fragment comprising VH, a CH1 domain, and a portion of a hinge region, and the portion of the hinge region includes cysteine residues configuring the S—S bond between heavy chains. F(ab')$_2$ fragment is a divalent antibody fragment in which two Fab' fragments are bound by an S—S bond between heavy chains in the hinge region.

<Anti-Human Fn14 Antibody of the Present Invention>

An anti-human Fn14 antibody or an antigen-binding fragment thereof of the present invention includes an anti-human Fn14 antibody or an antigen-binding fragment thereof having the following characteristics.

An anti-human Fn14 antibody or an antigen-binding fragment thereof comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 114 of SEQ ID NO: 2 and a light chain variable region comprising CDR1 consisting of the amino acid sequence of amino acid numbers 24 to 40 of SEQ ID NO: 4, CDR2 consisting of the amino acid sequence of amino acid numbers 56 to 62 of SEQ ID NO: 4, and CDR3 consisting of the amino acid sequence of amino acid numbers 95 to 103 of SEQ ID NO: 4.

In one embodiment, the anti-human Fn14 antibody or the antigen-binding fragment thereof of the present invention comprises a heavy chain variable region consisting of the amino acid sequence of amino acid numbers 1 to 125 of SEQ ID NO: 2 and a light chain variable region consisting of the amino acid sequence of amino acid numbers 1 to 114 of SEQ ID NO: 4.

In one embodiment, the anti-human Fn14 antibody or the antigen-binding fragment thereof of the present invention has the above-described characteristics, and further comprises a heavy chain constant region and a light chain constant region. As the constant region, any subclass constant region (for example, Igγ1, Igγ2, Igγ3, or Igγ4 as a heavy chain constant region, and Igλ or Igκ as a light chain constant region) can be selected. In one embodiment, the anti-human Fn14 antibody or the antigen-binding fragment thereof of the present invention comprises a human Igγ1 constant region as a heavy chain constant region and a human Igκ constant region as a light chain constant region.

The residue number related to the introduction of amino acid mutations in the constant region of the antibody used in the present specification can be defined according to the EU index (Kabat et al., 1991, Sequences of Proteins of Immunological Interest, 5th Ed., United States Public Health Service, National Institute of Health, Bethesda). L234A and L235A are substitutions of leucine at the amino acid 234 position and the amino acid 235 position with alanine in the human Igγ1 constant region according to the EU index of Kabat et al., respectively. Examples of the human Igγ1 constant region having amino acid mutations of L234A and L235A include a human Igγ1 constant region consisting of the amino acid sequence of amino acid numbers 126 to 455 of SEQ ID NO: 2.

In one embodiment, the anti-human Fn14 antibody of the present invention comprises a heavy chain consisting of the amino acid sequence represented by SEQ ID NO: 2 and a light chain consisting of the amino acid sequence represented by SEQ ID NO: 4.

It is known that when an antibody is expressed in cells, the antibody is modified after translation. Examples of the posttranslational modification include deletion of lysine at the C terminal of the heavy chain by a carboxypeptidase, modification of glutamine or glutamic acid at the N terminal of the heavy chain and the light chain to pyroglutamic acid by pyroglutamylation, glycosylation, oxidation, deamidation, and glycation, and it is known that such posttranslational modifications occur in various antibodies (Liu H et al., J Phar Sci. 2008, Vol. 97 No. 7, p. 2426-2447).

The anti-human Fn14 antibody or the antigen-binding fragment thereof of the present invention also includes an anti-human Fn14 antibody or an antigen-binding fragment thereof modified after translation. Examples of the anti-human Fn14 antibody or the antigen-binding fragment thereof of the present invention modified after translation include anti-human Fn14 antibodies which have undergone pyroglutamylation at the N terminal of the heavy chain variable region and/or deletion of lysine at the C terminal of the heavy chain, or antigen-binding fragments thereof. It is known in the field that such posttranslational modification due to pyroglutamylation at the N terminal or deletion of lysine at the C terminal does not have any influence on the activity of the antibody (Lyubarskaya Y et al., Anal Biochem. 2006, Vol. 348, p. 24-39).

In one embodiment, the anti-human Fn14 antibody of the present invention includes an antibody or an antigen-binding fragment thereof formed by posttranslational modification of an anti-human Fn14 antibody or an antigen-binding fragment thereof comprising a heavy chain variable region consisting of the amino acid sequence of amino acid numbers 1 to 125 of SEQ ID NO: 2 and a light chain variable region consisting of the amino acid sequence of amino acid numbers 1 to 114 of SEQ ID NO: 4.

In one embodiment, the posttranslational modification is pyroglutamylation at the N terminal of the heavy chain variable region and/or deletion of lysine at the C terminal of the heavy chain.

In one embodiment, the anti-human Fn14 antibody or the antigen-binding fragment thereof of the present invention comprises a heavy chain variable region consisting of the amino acid sequence of amino acid numbers 1 to 125 of SEQ ID NO: 2, in which glutamine of amino acid number 1 of SEQ ID NO: 2 is modified to pyroglutamic acid, and a light chain variable region consisting of the amino acid sequence of amino acid numbers 1 to 114 of SEQ ID NO: 4.

In one embodiment, the anti-human Fn14 antibody of the present invention is formed by posttranslational modification of an anti-human Fn14 antibody comprising a heavy chain consisting of the amino acid sequence represented by SEQ ID NO: 2 and a light chain consisting of the amino acid sequence represented by SEQ ID NO: 4, and the posttranslational modification is pyroglutamylation at the N terminal of the heavy chain and/or deletion of lysine at the C terminal of the heavy chain.

In one embodiment, the anti-human Fn14 antibody of the present invention comprises a heavy chain consisting of the amino acid sequence of amino acid numbers 1 to 454 of SEQ ID NO: 2, in which glutamine of amino acid number 1 of SEQ ID NO: 2 is modified to pyroglutamic acid, and a light chain consisting of the amino acid sequence of amino acid number 4.

In one embodiment, the antigen-binding fragment of the present invention is scFv, Fab, Fab', or F(ab')$_2$.

Any person skilled in the art can prepare a fused form in which the antibody or the antigen-binding fragment thereof is fused with another peptide or protein, or also can prepare a modified form to which a modifying agent is bound based on the present invention, and the antibody of the present invention also includes these forms of antibodies or antigen-binding fragments thereof. Other peptides or proteins used for the fusion are not particularly limited as long as the fused form binds to Fn14, and examples thereof include human serum albumin, various tag peptides, artificial helix motif peptide, maltose-binding proteins, glutathione S transferase, various toxins, and other peptides or proteins capable of promoting multimerization. The modifying agent used for the modification is not particularly limited as long as the modified form binds to Fn14, and examples thereof include polyethylene glycol, sugar chains, phospholipids, liposomes, and low-molecular compounds.

In one embodiment, the modifying agent used for the modification of the antibody or the antigen-binding fragment thereof of the present invention is polyethylene glycol.

The "anti-human Fn14 antibody" in the present specification means an antibody binding to human Fn14. Whether the anti-human Fn14 antibody binds to human Fn14 can be confirmed by using a known binding activity measurement method. Examples of the binding activity measurement method include an Enzyme-Linked ImmunoSorbent Assay (ELISA). In a case of using the ELISA, for example, a human Fn14 protein is immobilized on an ELISA plate and a test antibody is added thereto to be reacted. After the reaction, a secondary antibody such as an anti-IgG antibody, labeled with an enzyme such as horseradish peroxidase (HRP), is reacted. After the reaction, washing is performed, and then it is possible to confirm whether the test antibody binds to the human Fn14 by identifying binding of the secondary antibody through activity measurement using a reagent detecting the activity (for example, in a case of HRP labeling, TMB Microwell Peroxidase Substrate (Kirkegaard & Perry Laboratories, Inc., 50-76-03)). As a specific measurement method, the method described in Example 6 below can be used.

The anti-human Fn14 antibody of the present invention includes, in addition to binding to human Fn14, an antibody binding to Fn14 derived from other animals (for example, mouse Fn14), as long as the antibody binds to human Fn14.

The anti-human Fn14 antibody or the antigen-binding fragment thereof of the present invention can be easily prepared by a person skilled in the art using a known method in the field, based on sequence information on the heavy chain and the light chain of the antibody of the present invention, which is disclosed in the present specification. The anti-human Fn14 antibody or the antigen-binding fragment thereof of the present invention is not particularly limited, and can be produced according to the method described in the section of <Method for Producing Anti-Human Fn14 Antibody of the Present Invention, And Anti-Human Fn14 Antibody Produced by the Method> to be described later.

The anti-human Fn14 antibody or the antigen-binding fragment thereof of the present invention is further purified as needed, formulated according to a conventional method, and can be used for the prevention or treatment of inflammatory diseases such as excessive angiogenesis or wasting diseases such as weight loss, muscular wasting, and cachexia.

<Polynucleotide of the Present Invention>

A polynucleotide of the present invention includes a polynucleotide comprising a base sequence encoding the heavy chain variable region of the anti-human Fn14 antibody or the antigen-binding fragment thereof of the present invention and a polynucleotide comprising a base sequence encoding the light chain variable region of the anti-human Fn14 antibody or the antigen-binding fragment thereof of the present invention.

In one embodiment, the polynucleotide comprising a base sequence encoding the heavy chain variable region of the anti-human Fn14 antibody or the antigen-binding fragment thereof of the present invention is a polynucleotide comprising a base sequence encoding the heavy chain variable region consisting of the amino acid sequence of amino acid numbers 1 to 125 of SEQ ID NO: 2.

Examples of the polynucleotide comprising a base sequence encoding the heavy chain variable region shown by the amino acid sequence of amino acid numbers 1 to 125 of SEQ ID NO: 2 include a polynucleotide comprising a base sequence of base numbers 1 to 375 of SEQ ID NO: 1.

In one embodiment, the polynucleotide comprising a base sequence encoding the heavy chain variable region of the anti-human Fn14 antibody of the present invention comprises a base sequence encoding the heavy chain consisting of the amino acid sequence represented by SEQ ID NO: 2.

Examples of the polynucleotide comprising a base sequence encoding the heavy chain consisting of the amino acid sequence represented by SEQ ID NO: 2 include a polynucleotide comprising a base sequence represented by SEQ ID NO: 1.

In one embodiment, the polynucleotide comprising a base sequence encoding the light chain variable region of the anti-human Fn14 antibody or the antigen-binding fragment of the present invention comprises a base sequence encoding the light chain variable region consisting of the amino acid sequence of amino acid numbers 1 to 114 of SEQ ID NO: 4.

Examples of the polynucleotide comprising a base sequence encoding the light chain variable region consisting of the amino acid sequence of amino acid numbers 1 to 114 of SEQ ID NO: 4 include a polynucleotide comprising a base sequence of base numbers 1 to 342 of SEQ ID NO: 3.

In one embodiment, the polynucleotide comprising a base sequence encoding the light chain variable region of the anti-human Fn14 antibody of the present invention comprises a base sequence encoding the light chain consisting of the amino acid sequence represented by SEQ ID NO: 4.

Examples of the polynucleotide comprising a base sequence encoding the light chain consisting of the amino acid sequence represented by SEQ ID NO: 4 include a polynucleotide comprising a base sequence represented by SEQ ID NO: 3.

The polynucleotide of the present invention can be easily prepared by a person skilled in the art using a known method in the field based on the base sequence. For example, the polynucleotide of the present invention can be synthesized using a known gene synthesis method in the field. As the gene synthesis method, various methods such as a synthesis method of antibody genes described in WO90/07861 known by a person skilled in the art can be used.

<Expression Vector of the Present Invention>

An expression vector of the present invention includes an expression vector comprising a polynucleotide comprising a base sequence encoding the heavy chain variable region of the anti-human Fn14 antibody or the antigen-binding fragment thereof of the present invention, and/or a polynucleotide comprising a base sequence encoding the light chain variable region of the anti-human Fn14 antibody or the antigen-binding fragment thereof of the present invention.

In one embodiment, examples of the expression vector of the present invention include an expression vector comprising a polynucleotide comprising a base sequence encoding the heavy chain of the anti-human Fn14 antibody of the present invention, an expression vector comprising a polynucleotide comprising a base sequence encoding the light chain of the anti-human Fn14 antibody of the present invention, and an expression vector comprising a polynucleotide comprising a base sequence encoding the heavy chain of the anti-human Fn14 antibody of the present invention and a polynucleotide comprising a base sequence encoding the light chain of the antibody.

The expression vectors used to express the polynucleotide of the present invention are not particularly limited as long as a polynucleotide comprising a base sequence encoding the heavy chain variable region of the anti-human Fn14 antibody or the antigen-binding fragment thereof of the present invention and/or a polynucleotide comprising a base sequence encoding the light chain variable region of the anti-human Fn14 antibody or the antigen-binding fragment thereof of the present invention can be expressed in various host cells of eukaryotic cells (for example, animal cells, insect cells, plant cells, and yeast) and/or prokaryotic cells (for example, *Escherichia coli*), and the polypeptides encoded by these can be produced. Examples of the expression vector include plasmid vectors and viral vectors (for example, adenovirus or retrovirus). For example, pEE6.4 or pEE12.4 can be used. An antibody gene can also be expressed by introducing a variable region gene segment into an expression vector already having a human Ig constant region gene such as AG-γ1 and AG-κ (for example, see WO94/20632).

The expression vector of the present invention may comprise a promoter that is operably linked to the polynucleotide of the present invention. Examples of the promoter for expressing the polynucleotide of the present invention with an animal cell include a virus-derived promoter such as CMV, RSV, or SV40, an actin promoter, an EF (elongation factor) 1α promoter, and a heat shock promoter. Examples of the promoter for expressing the polynucleotide of the present invention by bacteria (for example, *Escherichia*) include a trp promoter, a lac promoter, a λPL promoter, and a tac promoter. Further, examples of the promoter for expressing the polynucleotide of the present invention by yeast include a GAL1 promoter, a GAL10 promoter, a PH05 promoter, a PGK promoter, a GAP promoter, and an ADH promoter.

In the case of using an animal cell, an insect cell, or yeast as the host cell, the expression vector of the present invention may comprise initiation codon and termination codon. In this case, the expression vector of the present invention may comprise an enhancer sequence, an untranslated region on the 5' side and the 3' side of genes encoding the antibody of the present invention or the heavy chain variable region or the light chain variable region thereof, a secretory signal sequence, a splicing junction, a polyadenylation site, or a replicable unit. In a case where *Escherichia coli* is used as the host cell, the expression vector of the present invention may comprise an initiation codon, a termination codon, a terminator region, and a replicable unit. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the purpose.

<Transformed Host Cell of the Present Invention>

Examples of the transformed host cell of the present invention include a host cell transformed with an expression vector comprising a polynucleotide comprising a base sequence encoding the heavy chain of the anti-human Fn14 antibody of the present invention and a polynucleotide comprising a base sequence encoding the light chain of the antibody, and a host cell transformed with an expression vector comprising a polynucleotide comprising a base sequence encoding the heavy chain of the anti-human Fn14 antibody of the present invention and an expression vector comprising a polynucleotide comprising a base sequence encoding the light chain of the antibody.

In one embodiment, the transformed host cell of the present invention includes a host cell transformed with the expression vector of the present invention, which is selected from the group consisting of the following (a) to (d):
 (a) a host cell transformed with an expression vector comprising a polynucleotide comprising a base sequence encoding the heavy chain variable region of the anti-human Fn14 antibody or the antigen-binding fragment thereof of the present invention and a polynucleotide comprising a base sequence encoding the light chain variable region of the antibody or the antigen-binding fragment thereof;
 (b) a host cell transformed with an expression vector comprising a polynucleotide comprising a base sequence encoding the heavy chain variable region of the anti-human Fn14 antibody or the antigen-binding fragment thereof of the present invention and an expression vector comprising a polynucleotide comprising a base sequence encoding the light chain variable region of the antibody or the antigen-binding fragment thereof;
 (c) a host cell transformed with an expression vector comprising a polynucleotide comprising a base sequence encoding the heavy chain variable region of the anti-human Fn14 antibody or the antigen-binding fragment thereof of the present invention; and
 (d) a host cell transformed with an expression vector comprising a polynucleotide comprising a base sequence encoding the light chain variable region of the anti-human Fn14 antibody or the antigen-binding fragment thereof of the present invention.

In one embodiment, the transformed host cell of the present invention includes a host cell transformed with the expression vector of the present invention, which is selected from the group consisting of the following (e) to (h):
 (e) a host cell transformed with an expression vector comprising a polynucleotide comprising a base sequence encoding the heavy chain of the anti-human Fn14 antibody of the present invention and a polynucleotide comprising a base sequence encoding the light chain of the antibody;
 (f) a host cell transformed with an expression vector comprising a polynucleotide comprising a base sequence encoding the heavy chain of the anti-human Fn14 antibody of the present invention and an expression vector comprising a polynucleotide comprising a base sequence encoding the light chain of the antibody;
 (g) a host cell transformed with an expression vector comprising a polynucleotide comprising a base sequence encoding the heavy chain of the anti-human Fn14 antibody of the present invention; and
 (h) a host cell transformed with an expression vector comprising a polynucleotide comprising a base sequence encoding the light chain of the anti-human Fn14 antibody of the present invention.

The transformed host cell is not particularly limited as long as the host cell is appropriate for the expression vector being used, transformed with the expression vector, and can express the antibody. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) and the like). For example, cultured cells such as CHO cells (CHO-K1SV cells and CHO-DG44 cells), 293 cells, and NS0 cells can be used.

A method for transforming the host cell is not particularly limited, and, for example, a calcium phosphate method or an electroporation method can be used.

<Method for Producing Anti-Human Fn14 Antibody of the Present Invention, and Anti-Human Fn14 Antibody Produced by the Method>

A method for producing the anti-human Fn14 antibody or the antigen-binding fragment thereof of the present invention includes a method for producing an anti-human Fn14 antibody or an antigen-binding fragment thereof, comprising a step of culturing a host cell selected from the group consisting of the following (A) to (C) to express the anti-human Fn14 antibody or the antigen-binding fragment thereof:

(A) a host cell transformed with an expression vector comprising a polynucleotide comprising a base sequence encoding the heavy chain variable region of the anti-human Fn14 antibody or the antigen-binding fragment thereof of the present invention and a polynucleotide comprising a base sequence encoding the light chain variable region of the antibody or the antigen-binding fragment thereof;

(B) a host cell transformed with an expression vector comprising a polynucleotide comprising a base sequence encoding the heavy chain variable region of the anti-human Fn14 antibody or the antigen-binding fragment thereof of the present invention and an expression vector comprising a polynucleotide comprising a base sequence encoding the light chain variable region of the antibody or the antigen-binding fragment thereof; and (C) a host cell transformed with an expression vector comprising a polynucleotide comprising a base sequence encoding the heavy chain variable region of the anti-human Fn14 antibody or the antigen-binding fragment thereof of the present invention, and a host cell transformed with an expression vector comprising a polynucleotide comprising a base sequence encoding the light chain variable region of the antibody or the antigen-binding fragment thereof.

In one embodiment, the method for producing the anti-human Fn14 antibody of the present invention includes a method for producing an anti-human Fn14 antibody, comprising a step of culturing a host cell selected from the group consisting of the following (D) to (F) to express the anti-human Fn14 antibody:

(D) a host cell transformed with an expression vector comprising a polynucleotide comprising a base sequence encoding the heavy chain of the anti-human Fn14 antibody of the present invention and a polynucleotide comprising a base sequence encoding the light chain of the antibody;

(E) a host cell transformed with an expression vector comprising a polynucleotide comprising a base sequence encoding the heavy chain of the anti-human Fn14 antibody of the present invention and an expression vector comprising a polynucleotide comprising a base sequence encoding the light chain of the antibody; and (F) a host cell transformed with an expression vector comprising a polynucleotide comprising a base sequence encoding the heavy chain of the anti-human Fn14 antibody of the present invention, and a host cell transformed with an expression vector comprising a polynucleotide comprising a base sequence encoding the light chain of the antibody.

The method for producing the anti-human Fn14 antibody or the antigen-binding fragment thereof of the present invention is not particularly limited as long as the method comprises a step of culturing the transformed host cell of the present invention to express the anti-human Fn14 antibody or the antigen-binding fragment thereof. In one embodiment, examples of the host cell used in the method include the host cells of (A) to (D) described above.

The transformed host cell can be cultured by a known method. Culture conditions, for example, the temperature, the pH of culture medium, and the culture time are appropriately selected. In a case where the host cell is an animal cell, examples of the culture medium include MEM culture medium supplemented with approximately 5% to 20% of fetal bovine serum (Eagle H, Science. 1959, Vol. 130, No. 3373, p. 432-437), DMEM culture medium (Dulbecco R and Freeman G, Virology. 1959, Vol. 8, p. 396-397), RPMI1640 culture medium (Moore G E et al., J Am Med Assoc. 1967, Vol. 199, p. 519), and 199 culture medium (Morgan J F et al., Proc Soc Exp Biol Med. 1950, Vol. 73, p. 1-8). The pH of the culture medium is preferably approximately 6 to 8, and the culture is generally performed at approximately 30° C. to 40° C. for approximately 15 to 336 hours under optional ventilation or stiffing. In a case where the host cell is an insect cell, as the culture medium, for example, Grace's culture medium (Smith G E et al., Proc Natl Acad Sci USA., 1985, Vol. 82, p. 8404) supplemented with fetal bovine serum can be used. The pH of the culture medium is preferably approximately 5 to 8, and the culture is generally performed at approximately 20° C. to 40° C. for approximately 15 hours to 100 hours under optional ventilation or stirring. In a case where the host cell is *Escherichia coli* or yeast, as the culture medium, for example, liquid culture medium supplemented with a source of nutrients is appropriate. The nutrient culture medium preferably includes a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is preferably approximately 5 to 8. In a case where the host cell is *Escherichia coli*, for example, LB culture medium or M9 culture medium (Mol. Clo., Cold Spring Harbor Laboratory, 2001, Vol. 3, A2.2) can be preferably used as the culture medium. The culture is generally performed at approximately 14° C. to 39° C. for approximately 3 to 24 hours under optional ventilation or stirring. In a case where the host cell is yeast, for example, Burkholder minimal medium (Bostian K A et al., Proc Natl Acad Sci USA. 1980, Vol. 77, p. 4504-4508) can be used as the culture medium. The culture is generally performed at approximately 20° C. to 35° C. for approximately 14 to 144 hours under optional ventilation or stirring. By performing the culture in the above-described manner, it is possible to express the anti-human Fn14 antibody or the antigen-binding fragment thereof of the present invention.

The method for producing the anti-human Fn14 antibody or the antigen-binding fragment thereof of the present invention may further comprise, in addition to the step of culturing the transformed host cell of the present invention to express the anti-human Fn14 antibody or the antigen-binding fragment thereof, a step of recovering, for example, isolating or purifying the anti-human Fn14 antibody or the antigen-binding fragment thereof from the transformed host cell and/or the culture supernatant. Examples of the isolation or purification method include methods using solubility such as salting-out and a solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing electrophoresis. For example, the antibody accumulated in a culture supernatant can be purified by various chromatographies, for example, column chromatography using Protein A column or Protein G column.

The anti-human Fn14 antibody or the antigen-binding fragment thereof of the present invention also includes an anti-human Fn14 antibody or an antigen-binding fragment thereof produced by the method for producing the anti-human Fn14 antibody or the antigen-binding fragment thereof of the present invention.

<Pharmaceutical Composition of the Present Invention>

A pharmaceutical composition of the present invention includes a pharmaceutical composition comprising the anti-human Fn14 antibody or the antigen-binding fragment thereof of the present invention, and a pharmaceutically acceptable excipient. The pharmaceutical composition of the present invention can be prepared by a method being generally used with excipients, that is, excipients for medicine or carriers for medicine being generally used in the field. Examples of dosage forms of the pharmaceutical compositions include parenteral drug such as an injection drug and a drip infusion drug, and these can be administered by intravenous administration, subcutaneous administration, intramuscular administration, or the like. In drug preparation, excipients, carriers, and additives in accordance with the dosage forms can be used within the pharmaceutically acceptable range.

The pharmaceutical composition of the present invention may comprise plural kinds of anti-human Fn14 antibodies or antigen-binding fragments thereof of the present invention. For example, the present invention also includes a pharmaceutical composition comprising an antibody or an antigen-binding fragment thereof that is not modified after translation, and an antibody or an antigen-binding fragment thereof formed by posttranslational modification of the antibody or the antigen-binding fragment thereof.

In one embodiment, the pharmaceutical composition of the present invention comprising the anti-human Fn14 antibody or the antigen-binding fragment thereof also includes the following pharmaceutical composition.

A pharmaceutical composition comprising an anti-human Fn14 antibody or an antigen-binding fragment thereof comprising a heavy chain variable region consisting of the amino acid sequence of amino acid numbers 1 to 125 of SEQ ID NO: 2 and a light chain variable region consisting of the amino acid sequence of amino acid numbers 1 to 114 of SEQ ID NO: 4, and an anti-human Fn14 antibody or an antigen-binding fragment thereof formed by posttranslational modification of the antibody or the antigen-binding fragment thereof.

The pharmaceutical composition of the present invention also includes a pharmaceutical composition comprising an antibody in which lysine at the C terminal of the heavy chain is deleted, an antibody or an antigen-binding fragment thereof modified after translation at the N terminal, an antibody in which lysine at the C terminal of the heavy chain is deleted and which is modified after translation at the N terminal, and/or an antibody which has lysine at the C terminal of the heavy chain and is not modified after translation at the N terminal.

In one embodiment, the pharmaceutical composition of the present invention comprising the anti-human Fn14 antibody also includes a pharmaceutical composition comprising two or more kinds of anti-human Fn14 antibodies among the following (5) to (8):

(5) an anti-human Fn14 antibody comprising a heavy chain consisting of the amino acid sequence of amino acid numbers 1 to 454 of SEQ ID NO: 2 and a light chain consisting of the amino acid sequence represented by SEQ ID NO: 4.

(6) an anti-human Fn14 antibody comprising a heavy chain consisting of the amino acid sequence represented by SEQ ID NO: 2, in which glutamine of amino acid number 1 of SEQ ID NO: 2 is modified to pyroglutamic acid, and a light chain consisting of the amino acid sequence represented by SEQ ID NO: 4.

(7) an anti-human Fn14 antibody comprising a heavy chain consisting of the amino acid sequence of amino acid numbers 1 to 454 of SEQ ID NO: 2, in which glutamine of amino acid number 1 of SEQ ID NO: 2 is modified to pyroglutamic acid, and a light chain consisting of the amino acid sequence represented by SEQ ID NO: 4.

(8) an anti-human Fn14 antibody comprising a heavy chain consisting of the amino acid sequence represented by SEQ ID NO: 2 and a light chain consisting of the amino acid sequence represented by SEQ ID NO: 4.

In one embodiment, the pharmaceutical composition of the present invention comprising the anti-human Fn14 antibody or the antigen-binding fragment thereof also includes the following pharmaceutical composition. A pharmaceutical composition comprising an anti-human Fn14 antibody comprising a heavy chain consisting of the amino acid sequence represented by SEQ ID NO: 2 and a light chain consisting of the amino acid sequence represented by SEQ ID NO: 4, an anti-human Fn14 antibody comprising a heavy chain consisting of the amino acid sequence of amino acid numbers 1 to 454 of SEQ ID NO: 2, in which glutamine of amino acid number 1 of SEQ ID NO: 2 is modified to pyroglutamic acid, and a light chain consisting of the amino acid sequence represented by SEQ ID NO: 4, and a pharmaceutically acceptable excipient.

The amount of the anti-human Fn14 antibody or the antigen-binding fragment thereof of the present invention to be added in formulation varies depending on the degree of a patient's symptoms, the age of a patient, a dosage form of the drug to be used, the binding titer of the antibody, or the like, and for example, the antibody or the antigen-binding fragment thereof can be used in an amount of approximately 0.001 mg/kg to 100 mg/kg during administration.

The pharmaceutical composition of the present invention can be used as an agent for preventing or treating diseases such as cancer cachexia in which active human Fn14 is involved in pathogenesis.

The present invention includes a pharmaceutical composition for preventing or treating cancer cachexia, comprising the anti-human Fn14 antibody or the antigen-binding fragment thereof of the present invention. Further, the present invention includes a method for treating or preventing cancer cachexia, comprising a step of administering a therapeutically effective amount of the anti-human Fn14 antibody or the antigen-binding fragment thereof of the present invention. Further, the present invention includes the anti-human Fn14 antibody or the antigen-binding fragment thereof of the present invention for use in preventing or treating cancer cachexia. Further, the present invention includes use of the anti-human Fn14 antibody or the antigen-binding fragment thereof of the present invention for the manufacturing of a pharmaceutical composition for preventing or treating cancer cachexia.

The present invention provides a pharmaceutical composition for preventing or treating cancer or cancer cachexia, which comprises the anti-human Fn14 antibody or the antigen-binding fragment thereof of the present invention and is used in combination with an anticancer agent. The present invention provides a method for preventing or treating cancer or cancer cachexia, which comprises a step of administering effective amounts of the anti-human Fn14 antibody or the antigen-binding fragment thereof of the present invention and an anticancer agent. The present invention provides the anti-human Fn14 antibody or the antigen-binding fragment thereof of the present invention which is used in combination with an anticancer agent for use in the prevention or treatment of cancer or cancer cachexia. The present invention provides use of the anti-human Fn14 antibody or the antigen-binding fragment thereof of the present invention for the manufacturing of a pharmaceutical composition for preventing or treating cancer or cancer cachexia, and use of the pharmaceutical composition in combination with an anticancer agent.

The present invention provides a pharmaceutical composition for preventing or treating cancer or cancer cachexia, which comprises an anticancer agent and is used in combination with the anti-human Fn14 antibody or the antigen-binding fragment thereof of the present invention. The present invention provides an anticancer agent which is used in combination with the anti-human Fn14 antibody or the antigen-binding fragment thereof of the present invention for use in preventing or treating cancer or cancer cachexia. The present invention provides use of an anticancer agent for the manufacturing of a pharmaceutical composition for preventing or treating cancer or cancer cachexia, and use of the pharmaceutical composition in combination with the anti-human Fn14 antibody or the antigen-binding fragment thereof of the present invention.

In one embodiment, the anticancer agent used in the present invention is gemcitabine.

For better understanding regarding the present invention, specific examples referred to will be provided, but these are merely examples and the present invention is not limited thereto.

EXAMPLES

With regard to parts using commercially available kits or reagents, experiments were performed according to the accompanying protocol unless otherwise noted.

Example 1

Acquisition of Human and Mouse Fn14-Fc Fusion Proteins

The inventors prepared a human Fn14-human Fc fusion protein and a mouse Fn14-mouse Fc fusion protein for use as an antigen for acquiring an anti-Fn14 antibody and a material to be used in a screening test. The human Fn14-human Fc fusion protein is a fusion protein in which the C terminal of the extracellular partial sequence of a human Fn14 sequence (1st to 79th amino acids of NCBI accession number: NP_057223.1) and the N terminal of the human Fc region (106th to 330th amino acids of NCBI accession number: P01857.1) are linked by a peptide linker (SEQ ID NO: 9). The mouse Fn14-mouse Fc fusion protein is a fusion protein in which the C terminal of the extracellular partial sequence of a mouse Fn14 sequence (1st to 75th amino acid of NCBI accession number: AAF07882.1) and the N terminal of the mouse Fc region are linked, and specifically, a fusion protein in which genes encoding the extracellular partial sequence of the mouse Fn14 sequence are incorporated into the multicloning site between the hEF1-HTLV promoter region and the mIgG2B-Fc region of pFUSE-mIgG2B-Fc1 (InvivoGen, pfuse-mg2bfc 1) using restriction enzymes EcoRI and EcoRV and expressed. Expression vectors in which genes encoding the above-described fusion proteins were incorporated into a GS vector pEE12.4 (Lonza) were prepared and introduced into CHO-K1SV cells (Lonza), respectively. The human Fn14-human Fc fusion protein and the mouse Fn14-mouse Fc fusion protein were each purified from the culture supernatant of the CHO-K1SV cells according to a conventional method.

Example 2

Acquisition of Anti-Human Fn14 Antibody

An antibody was prepared using a human monoclonal antibody developing technology "VelocImmune" (VelocImmune antibody technology: Regeneron Pharmaceuticals, Inc. (U.S. Pat. No. 6,596,541)) mouse. The antibody obtained by the VelocImmune technology is an antibody (also referred to as a chimeric antibody) having a variable region of a human antibody and a constant region of a mouse antibody. VelocImmune mice were immunized with an adjuvant for causing an immune reaction together with a human Fn14 protein in which a human Fe region was cut and removed from the human Fn14-human Fe fusion protein prepared in Example 1 using FabRICATOR (Sigma, 77661). Lymphocytes collected from the lymph node of the immunized mouse were fused with mouse-derived myeloma cells SP2/0-Ag14 (ATCC: CRL-1581) according to a conventional method to prepare hybridomas, and the hybridomas were monocloned. Hybridomas producing an antibody, which binds to human Fn14 and suppresses the NFkB activation induced by Tweak stimulation (hereinafter, referred to as "Tweak-induced NFkB activation" in Examples below), were selected, and the antibody was purified.

Example 3

NFkB Activation Assay

In order to evaluate the agonist action of the antibody found in Example 2 on human Fn14, the action of the antibody on NFkB activation in the absence of Tweak was evaluated by reporter assay. Specifically, HEK293 cells (ATCC, CRL-1573) into which a luciferase reporter vector pGL4.32 (Promega K. K., E8491) having an NFkB transcription responsive element incorporated thereinto was stably introduced (hereinafter, referred to as NFkB/HEK293 cells) were prepared and used for evaluation.

The NFkB/HEK293 cells were suspended in 10% fetal bovine serum-containing DMEM (Sigma, D6429) at 1.25×

10⁵ cells/mL, and seeded at 80 µL/well in a clear bottom white 96-well plate (Corning Incorporated, 3610). After culture for 2 hours in a $CO_2$ incubator set at 37° C. with an atmosphere of 5% $CO_2$, a 12-step dilution series of the purified antibody obtained in Example 2 was prepared in the above culture medium with about 3-fold common ratio from a final concentration of 1 ng/mL to 300 µg/mL, and then added at 20 µL/well. After overnight culture at 37° C. with 5% $CO_2$, a luciferase expression was measured using a luciferase measurement reagent ONE-Glo Luciferase Assay System (Promega Corporation) to quantify the NFkB activation.

As a result, an anti-human Fn14 antibody which did not induce the NFkB activation, that is, did not exhibit agonist activity, was selected and named 4-1.

Example 4

Preparation of Fully Humanized Antibody and Murinized Antibody

Genes encoding the heavy chain and the light chain of the antibody were cloned from the hybridomas producing the antibody selected in Example 3, and the sequence was determined. After the determination of the antibody sequence, genes encoding signal sequences (Wittle N et al., Protein Engineering. 1987, Vol. 1, No. 6, p. 499-505) and human Igγ1 constant region genes (consisting of the base sequence of base numbers 376 to 1365 of SEQ ID NO: 1) having amino acid mutations of L234A and L235A were respectively ligated to the 5' side and the 3' side of the heavy chain variable region genes, and the heavy chain genes were inserted into a GS vector pEE6.4 (Lonza). In addition, genes encoding signal sequences (Wittle N et al., Protein Engineering. 1987, Vol. 1, No. 6, p. 499-505) and constant region genes (consisting of the base sequence of base numbers 343 to 660 of SEQ ID NO: 3) of a human κ chain were respectively ligated to the 5' side and the 3' side of the light chain variable region genes, and the light chain genes were inserted into a GS vector pEE12.4. These GS vectors were subjected to restriction enzyme fragmentation with NotI-HF and PvuI-HF, and ligated using DNA Ligation Kit <Mighty Mix> (Takara Bio Inc., 6023) to form a GS vector in which both the heavy chain genes and the light chain genes were inserted. The antibody was purified according to a conventional method from the culture supernatant of CHO-K1SV cells obtained by transfecting the vector, and thus a fully humanized antibody of 4-1 was acquired and named 4-1h.

The base sequence of the heavy chain of 4-1h prepared is represented by SEQ ID NO: 1, the amino acid sequence encoded thereby is represented by SEQ ID NO: 2, the base sequence of the light chain is represented by SEQ ID NO: 3, and the amino acid sequence encoded thereby is represented by SEQ ID NO: 4. The variable region of the heavy chain represented by SEQ ID NO: 2 consists of the amino acid sequence of amino acid numbers 1 to 125 of SEQ ID NO: 2, and the variable region of the light chain represented by SEQ ID NO: 4 consists of the amino acid sequence of amino acid numbers 1 to 114 of SEQ ID NO: 4. CDR1, CDR2, and CDR3 of the heavy chain variable region of 4-1h consist of the amino acid sequences of amino acid numbers 31 to 35, 50 to 65, and 98 to 114 of SEQ ID NO: 2, respectively. CDR1, CDR2, and CDR3 of the light chain variable region of 4-1h consist of the amino acid sequences of amino acid numbers 24 to 40, 56 to 62, and 95 to 103 of SEQ ID NO: 4, respectively.

A murinized antibody of 4-1h (hereinafter, referred to as 4-1m) was prepared to reduce the immunogenic risk in the evaluation of the anti-human Fn14 antibody by a mouse in vivo test. A base sequence encoding the variable region of 4-1m was prepared by partially substituting the framework region (FR) of the light chain and the heavy chain of 4-1h with FR of other mouse antibodies.

4-1m was obtained using the same method as the vector formation, antibody expression, and purification for 4-1h described above. For the constant region of the heavy chain, genes encoding mouse Igγ2a constant region genes (consisting of the base sequence of base numbers 376 to 1365 of SEQ ID NO: 5) having a D265A amino acid mutation are used, and for the constant region of the light chain, constant region genes (consisting of the base sequence of base numbers 343 to 660 of SEQ ID NO: 7) of a mouse κ chain were used.

The base sequence of the heavy chain of 4-1m prepared is represented by SEQ ID NO: 5, the amino acid sequence encoded thereby is represented by SEQ ID NO: 6, the base sequence of the light chain is represented by SEQ ID NO: 7, and the amino acid sequence encoded thereby is represented by SEQ ID NO: 8. The variable region of the heavy chain represented by SEQ ID NO: 6 consists of the amino acid sequence of amino acid numbers 1 to 125 of SEQ ID NO: 6, and the variable region of the light chain represented by SEQ ID NO: 8 consists of the amino acid sequence of amino acid numbers 1 to 114 of SEQ ID NO: 8. CDR1, CDR2, and CDR3 of the heavy chain variable region of 4-1m consist of the amino acid sequences of amino acid numbers 31 to 35, 50 to 65, and 98 to 114 of SEQ ID NO: 6, respectively. CDR1, CDR2, and CDR3 of the light chain variable region of 4-1m consist of the amino acid sequences of amino acid numbers 24 to 40, 56 to 62, and 95 to 103 of SEQ ID NO: 8, respectively.

Example 5

Amino Acid Modification Analysis of Fully Humanized Antibody 4-1h purified was subjected to amino acid modification analysis, and as a result, most of the purified antibodies had pyroglutamylation at the N terminal of the heavy chain and deletion of lysine at the C terminal.

Example 6

Human and Mouse Fn14 Binding ELISA of Fully Humanized Antibody and Murinized Antibody Binding activities of 4-1h and 4-1m acquired in Example 4 to a Fn14 protein were evaluated. The human Fn14-human Fc fusion protein and the mouse Fn14-mouse Fc fusion protein acquired in Example 1 were diluted in phosphate buffered saline (PBS) at 1 µg/mL and added to a MaxiSorp 384-well transparent plate (Nunc, 464718) at 15 µL/well. Incubation was performed overnight at 4° C. for Immobilization. On the next day, the solid phase liquid was removed, and washing was performed with a 0.05% Tween-20-containing Tris-buffered saline (TBS-T). PBS containing 20% Blocking One (Nacalai tesque, Inc., 03953-95) was added thereto at 50 µL/well. The resultant was left at room temperature for 1 hour, and then washed with TBS-T. A dilution series of 4-1h or 4-1m acquired in Example 4 was prepared by dilution in 12 steps with a 4-fold common ratio from a maximum concentration of 30 µg/mL using TBS-T containing 5% Blocking One (hereinafter, referred to as a diluent), and added at 20 µL/well. After incubation for 1 hour at room temperature, washing was performed with TBS-T. A horseradish peroxidase-labeled anti-human kappa light chain antibody (SouthernBiotech, 2060-05) as a secondary antibody diluted 5000 times with a diluent was added at 20 μL/well for detection of 4-1h, and a horseradish peroxidase-labeled anti-mouse kappa light chain antibody (SouthernBiotech, 1050-05) as a secondary antibody diluted 4000 times with a diluent was added at 20 μL/well for detection of 4-1m. After incubation for 1 hour at room temperature, washing was performed with TBS-T. A TMB Microwell Peroxidase Substrate (Kirkegaard & Perry Laboratories, Inc., 50-76-03) was added, and the resultant was left for 3 minutes in the evaluation of 4-1h, or left for 5 minutes in the evaluation of 4-1m. Then, the reaction was stopped by adding a 2M sulfuric acid, and the absorbance at 450 nm was measured with SpectraMax Paradigm (Molecular Devices, LLC). The test was performed in duplicate, and $EC_{50}$ values were calculated by 4-parameter logistic curve fitting.

As a result, 4-1h and 4-1m prepared in Example 4 were confirmed to have binding activity to the human Fn14 and the mouse Fn14 (Table 1).

Table 1: Binding Activities of 4-1h and 4-1m to Human Fn14 and Mouse Fn14

TABLE 1

| Antibody Name | $EC_{50}$ (ng/mL) | |
| --- | --- | --- |
|  | Human | Mouse |
| 4-1h | 30.4 | 23.2 |
| 4-1m | 18.2 | 16.5 |

Example 7

Tweak-Induced NFkB Activation Inhibition Assay for Fully Humanized Antibody

In order to evaluate the antagonist activity of 4-1h acquired in Example 4 against Fn14, a Tweak-induced NFkB activation inhibitory action was evaluated by reporter assay.

NFkB/HEK293 cells prepared in Example 3 were suspended in 10% fetal bovine serum-containing DMEM at $1.25 \times 10^5$ cells/mL, and seeded at 80 μL/well in a clear bottom white 96-well plate. After overnight culture at 37° C. with 5% $CO_2$, a 11-step dilution series of 4-1h obtained in Example 4 was prepared in the above culture medium with about 3-fold common ratio from a final concentration of 0.1 ng/mL to 10 μg/mL, and then added at 10 μL/well. After culture for 30 minutes at 37° C. with 5% $CO_2$, 10 μL of Tweak (PeproTech, Inc., 310-06) was added so that a final concentration was 100 ng/mL. After culture for 5 hours at 37° C. with 5% $CO_2$, the NFkB activation was quantified according to the method for Example 3. A group in which only an antibody-free culture medium was added was set as a control group, a Tweak-added group was defined as 0% inhibition, and a non-Tweak-added group was defined as 100% inhibition to calculate a 50% inhibition concentration ($IC_{50}$ value) of the antibody by 4-parameter logistic curve fitting. The antibodies were tested in duplicate, and $IC_{50}$ values in the three trials were geometrically averaged to calculate a 95% confidence interval (Table 2). In this test, a mouse anti-human Fn14 antibody CRCBT-06-002 (Patent Document 2) was used as a comparative antibody.

As a result, it has been found that 4-1h has stronger antagonist activity than CRCBT-06-002.

Table 2: Inhibitory Activity of 4-1h with respect to Tweak-Induced NFkB Activation

TABLE 2

| Antibody Name | $IC_{50}$ (ng/mL) (95% confidence interval) |
| --- | --- |
| 4-1h | 41.5 |
|  | (27.2-63.4) |
| CRCBT-06-002 | 115 |
|  | (72.7-183) |

Example 8

IL-8 Production Assay for Fully Humanized Antibody

The functional activity of 4-1h acquired in Example 4 was evaluated by an in vitro IL-8 production assay. A375 cells (ATCC, CRL-1619) were suspended in 10% fetal bovine serum-containing DMEM at $5 \times 10^4$ cells/mL, and seeded at 100 μL/well in a 96-well flat bottom plate (IWAKI CO., LTD., 3860-096). After overnight culture at 37° C. with 5% $CO_2$, washing was performed with PBS. A 10-fold dilution series of 4-1h obtained in Example 4 was prepared to a final concentration of 1 ng/mL to 100 μg/mL in the above culture medium, and added to the cells. After overnight culture at 37° C. with 5% $CO_2$ in the presence of Tweak with a final concentration of 5 ng/mL (antagonist activity evaluation) or in the absence of Tweak (agonist activity evaluation), the culture supernatant was collected, and the IL-8 concentration in the culture supernatant was measured using a Human IL-8/CXCL8 Quantikine ELISA kit (R&D Systems, D8000C). The final volumes in the antagonist activity evaluation and the agonist activity evaluation were 65 μL/well and 100 μL/well in the experiments, respectively. In this test, the antibodies were tested in duplicate using CRCBT-06-002 as a comparative antibody.

In the antagonist activity evaluation, a group in which only an antibody-free culture medium was added was set as a control group, a Tweak-added group was defined as 0% inhibition, and a non-Tweak-added group was defined as 100% inhibition to calculate an inhibition rate. Arithmetic mean of maximum inhibition rates±standard error in each of four experiments is shown in Table 3 (Table 3). A graph of antagonist activity is shown in FIG. 1, and a graph of agonist activity is shown in FIG. 2.

Figure 2:
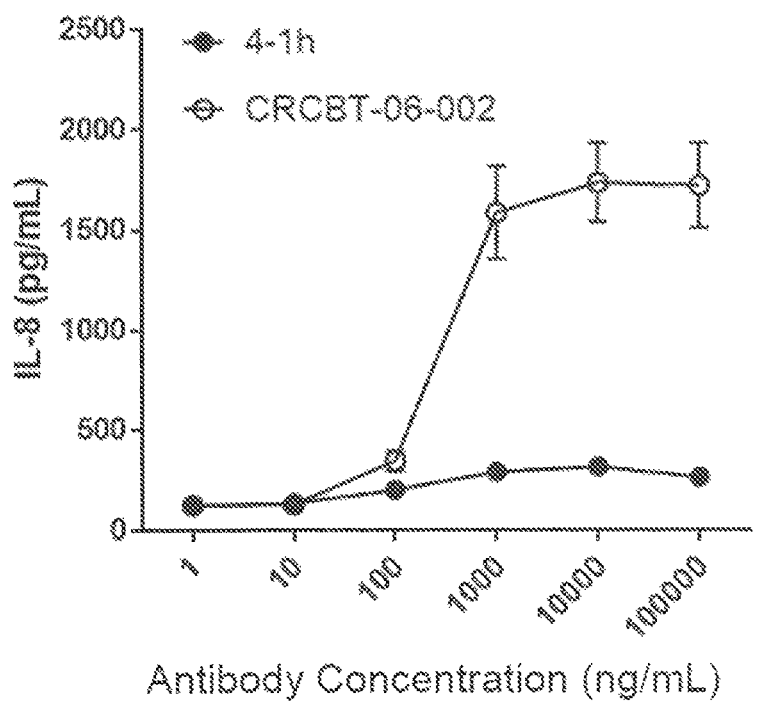
FIG. 2 shows an IL-8 secretion induced by anti-human Fn14 antibody stimulation in A375 cells. The vertical axis represents an IL-8 concentration (pg/mL), and the horizontal axis represents an antibody concentration (ng/mL).

As shown in Table 3 and FIG. 1, it has been found that 4-1h exhibits almost complete inhibitory activity with respect to IL-8 production induced by Tweak stimulation, whereas CRCBT-06-002 exhibits only partial inhibitory activity. In addition, as shown in FIG. 2, CRCBT-06-002 induced IL-8 production by itself in the absence of Tweak, whereas 4-1h of the present invention hardly induced IL-8 production.

From the above, it has been found that CRCBT-06-002 is a partial antagonist antibody having an agonist action, whereas 4-1h is a complete antagonist antibody having few agonist action on human Fn14.

Table 3: Inhibitory Activities of 4-1h and CRCBT-06-002 with respect to IL-8 Production Induced by Tweak Stimulation

TABLE 3

| Antibody Name | Maximum Inhibition Rates (%) Mean ± Standard Error |
|---|---|
| 4-1h | 96.4 ± 0.4 |
| GRCBT-06-002 | 53.0 ± 6.8 |

Example 9

Action in Mouse Model of Cancer Cachexia

Mice bearing the mouse colon cancer cell line C26 (COLON 26) are one of the representative cancer cachexia models showing weight decrease and a reduction in the muscle mass, that are characteristics of cachexia (Aulino P et al., BCM Cancer. 2010, Vol. 10 363, p. 1-15) (Bonetto A et al., J Vis Exp. 2016, November 30 117, p. 1-21).

C26 cells (National Cancer Institute) suspended at $10^6$ cells/100 µL using BD Matrigel Matrix Basement membrane Phenol-red Free (BD, 356237) were subcutaneously injected in an amount of 100 µL into male CD2F1 mouse (Charles River Laboratories Japan Inc.) to prepare C26 tumor-bearing mouse. After confirming that the body weight of the C26 tumor-bearing mouse began to decrease, antibody administration was started. Specifically, 4-1m diluted with PBS was subcutaneously administered to the C26 tumor-bearing mouse at 3 mg/kg (dosage: 10 mL/kg) on the 25th, 28th, 30th, 32nd, and 35th days after cell injection. An isotype control antibody was administered to the control group in the same manner. A mouse IgG2a antibody against keyhole limpet hemocyanin (KLH), which is an antigen that does not exist in the biological body, was acquired and used according to a conventional method as the isotype control antibody. The administration was started with 15 mice in each group. Two mice in the 4-1m administration group and seven mice in the control group died by the 37th day which was the end of the experiment.

On the day before the end of the experiment (36th day), a grip strength was measured using a small animal grip strength measuring device (MELQUEST Co., Ltd., GPM-100B). The body weight was measured on the 37th day, and the weight of the isolated tibialis anterior was measured as the muscle mass. Regarding the indices measured on the 36th day and the 37th day, a significant difference between the 4-1m administration group and the control group was determined using Student's t-test. In all cases, p<0.05 was considered significant, and in a case where there was a significant difference, a symbol (*) was placed in the graph (the symbol ** in the graph indicates that there was a significant difference because of p<0.01).

Figure 3:
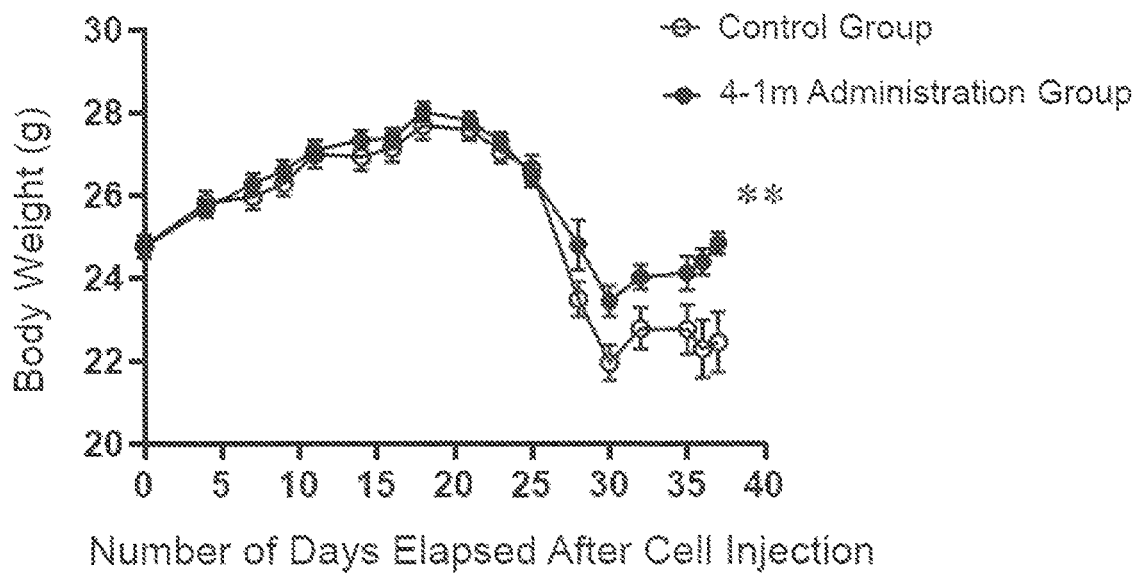
FIG. 3 shows an inhibitory effect of a murinized anti-human Fn14 antibody 4-1m on weight loss induced by transplanting mouse colon cancer cell line C26 cells into mice. The vertical axis represents a body weight (g), and the horizontal axis represents the number of days elapsed after cancer cell injection.
Figure 4:
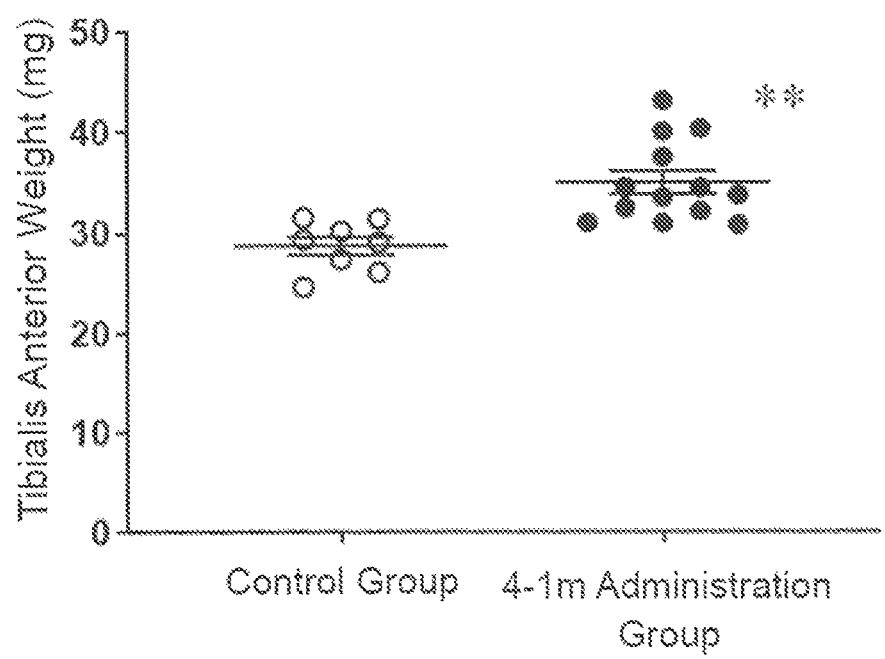
FIG. 4 shows an inhibitory effect of the murinized anti-human Fn14 antibody 4-1m on a decrease in the muscle mass induced by transplanting mouse colon cancer cell line C26 cells into mice. The vertical axis represents the weight (mg) of the tibialis anterior.
Figure 5:
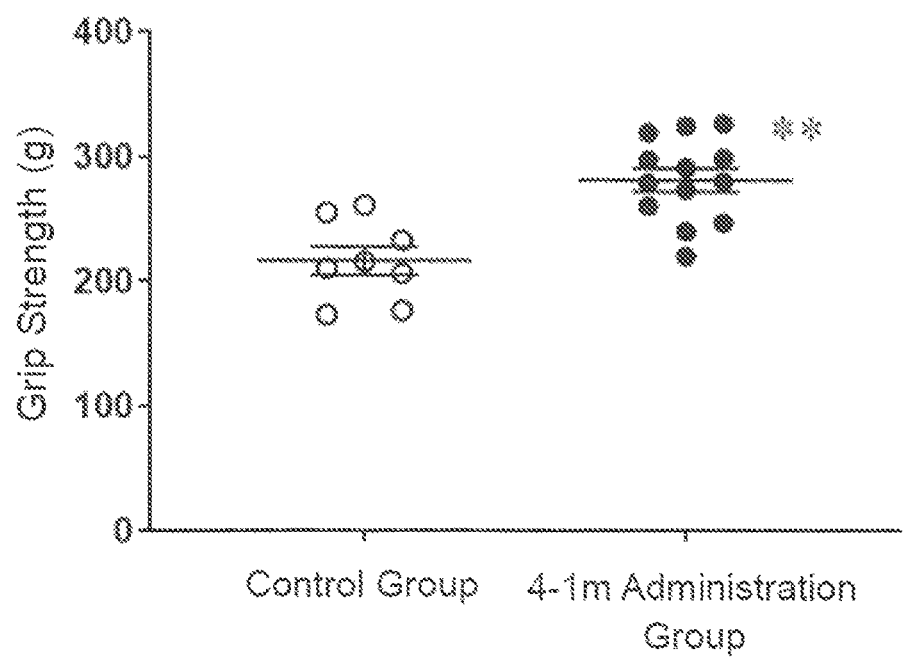
FIG. 5 shows an inhibitory effect of the murinized anti-human Fn14 antibody 4-1m on a decrease in the muscle function induced by transplanting mouse colon cancer cell line C26 cells into mice. The vertical axis represents a grip strength (g).

Body weight changes successively measured up to the 37th day are shown in FIG. 3. The weight decrease progressed even after the start of administration in the control group. However, the weight decrease was suppressed in the 4-1m administration group, and on the 37th day, a significant weight increase was observed in the 4-1m administration group compared to the control group (P=0.0019). In addition, a muscle mass increase was observed in the 4-1m administration group (FIG. 4, p=0.0009). Furthermore, the grip strength also significantly increased (FIG. 5, p=0.0003) in the 4-1m administration group, and an improvement was shown not only in the muscle mass but also in the muscle function.

The above results showed that 4-1m is effective against cachexia and may be effective even in therapeutic administration after observation of weight decrease.

Example 10

Action on Survival Period in Mouse Model of Cancer Cachexia

C26 tumor-bearing mice were prepared in the same manner as in Example 9. Administration was started with 5 mice in each group from a time when the body weight of the C26 tumor-bearing mouse began to decrease. Specifically, 4-1m diluted with PBS was subcutaneously administered at 0.3 mg/kg (dosage: 10 mL/kg) three times a week from the 22th to 70th days after cell injection, and then on the 71th, 76th, 78th, 83th, and 85th days. The same isotype control antibody as in Example 9 was administered to the control group in the same manner as in 4-1m. Gemcitabine (trade name: GEMZAR, Eli Lilly and Company) diluted with PBS was subcutaneously administered to the gemcitabine administration group at 10 mg/kg (dosage: 10 mL/kg). Both 4-1m and gemcitabine were administered to the gemcitabine-4-1m combination administration group on the same day. A long diameter and a short diameter of the tumor were successively measured using calipers (ASONE, VC01-150), and the tumor volume was calculated with the following formula.

Tumor Volume=Long Diameter (mm)×Short Diameter (mm)×Short Diameter (mm)/2

Figure 6:
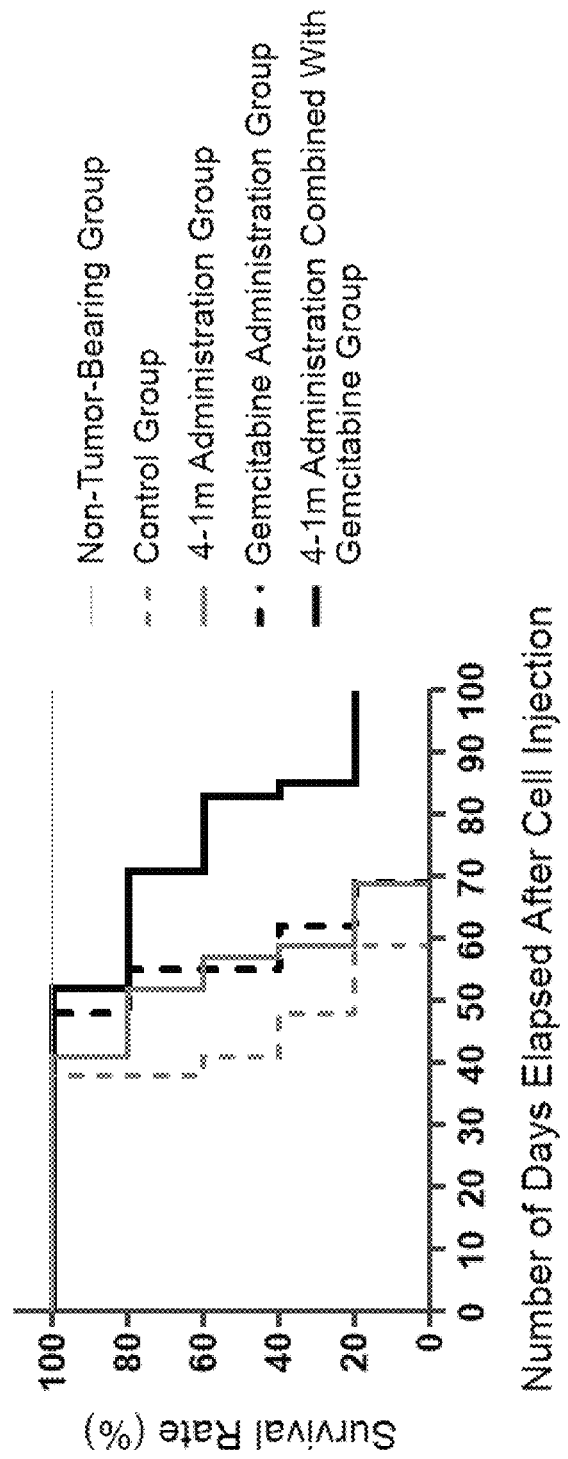
FIG. 6 shows an effect of the murinized anti-human Fn14 antibody 4-1m in combination with gemcitabine on the survival period of mice transplanted with mouse colon cancer cell line C26 cells. The vertical axis represents the survival rate (%), and the horizontal axis represents the number of days elapsed after cancer cell injection.

Survival rates of the mice are shown as Kaplan-Meier survival curves in FIG. 6. In a case where differences in the survival curves between the groups are compared, a logrank test was performed, and p<0.05 was considered significant. The median survival periods of the control group, the 4-1m administration group, and the gemcitabine administration group were 41 days, 57 days, and 55 days, respectively. The median survival period of the gemcitabine-4-1m combination administration group was 83 days, and a significant difference was observed compared to the survival curve of the 4-1m alone or gemcitabine alone administration group.

Figure 7:
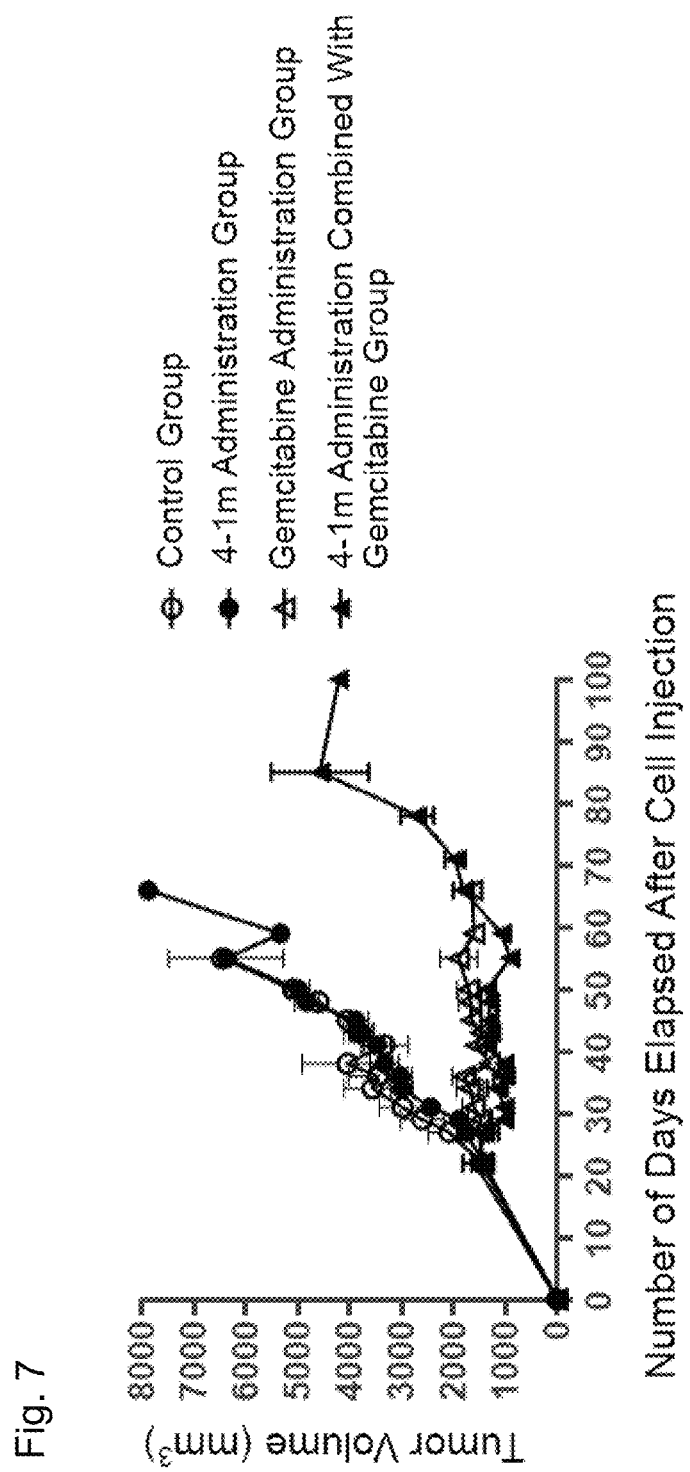
FIG. 7 shows an effect of combined use of the murinized anti-human Fn14 antibody 4-1m with gemcitabine on the volume of the tumor formed by transplanting mouse colon cancer cell line C26 cells into mice. The vertical axis represents the tumor volume ($mm^3$), and the horizontal axis represents the number of days elapsed after cancer cell injection.

In both the case where the antibody was administered alone and the case where the antibody was administered in combination with the gemcitabine, there was no influence of the administration of 4-1m on the tumor volume (FIG. 7).

The above results showed that 4-1m may prolong the survival period without affecting the tumor size, and be more effective in improving the survival rate by using in combination with anticancer agents such as gemcitabine.

INDUSTRIAL APPLICABILITY

The anti-human Fn14 antibody of the present invention is useful for preventing or treating various diseases in which human Fn14 is involved in pathogenesis. In addition, the method for producing a polynucleotide, an expression vector, a transformed host cell, or an antibody of the present invention is expected to be useful for producing the anti-human Fn14 antibody.

Sequence List Free Text

In the number heading <223> of the following sequence list, description of "Artificial Sequence" is made. Specifically, the base sequences represented by SEQ ID NOS: 1, 3, 5, and 7 of the sequence list are respectively the base sequences of the heavy chain and the light chain of the anti-human Fn14 antibody, and the amino acid sequences represented by SEQ ID NOS: 2, 4, 6, and 8 are respectively the amino acid sequences of the heavy chain and the light chain encoded by SEQ ID NOS: 1, 3, 5, and 7. The amino acid sequence represented by SEQ ID NO: 9 is the peptide linker sequence linking a human Fn14 protein and a human Fc region protein.

The invention claimed is:

1. An anti-human Fn14 antibody or an antigen-binding fragment thereof comprising:
a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 114 of SEQ ID NO: 2; and
a light chain variable region comprising CDR1 consisting of the amino acid sequence of amino acid numbers 24 to 40 of SEQ ID NO: 4, CDR2 consisting of the amino acid sequence of amino acid numbers 56 to 62 of SEQ ID NO: 4, and CDR3 consisting of the amino acid sequence of amino acid numbers 95 to 103 of SEQ ID NO: 4.

2. The anti-human Fn14 antibody or the antigen-binding fragment thereof according to claim 1, selected from:
an anti-human Fn14 antibody or an antigen-binding fragment thereof comprising a heavy chain variable region consisting of the amino acid sequence of amino acid numbers 1 to 125 of SEQ ID NO: 2 and a light chain variable region consisting of the amino acid sequence of amino acid numbers 1 to 114 of SEQ ID NO: 4; and
an anti-human Fn14 antibody or an antigen-binding fragment thereof comprising a heavy chain variable region consisting of the amino acid sequence of amino acid numbers 1 to 125 of SEQ ID NO: 2 and a light chain variable region consisting of the amino acid sequence of amino acid numbers 1 to 114 of SEQ ID NO: 4, wherein the antibody or antigen-binding fragment thereof comprises a posttranslational modification.

3. The anti-human Fn14 antibody or the antigen-binding fragment thereof according to claim 2, comprising:
a heavy chain variable region consisting of the amino acid sequence of amino acid numbers 1 to 125 of SEQ ID NO: 2; and
a light chain variable region consisting of the amino acid sequence of amino acid numbers 1 to 114 of SEQ ID NO: 4.

4. The anti-human Fn14 antibody or the antigen-binding fragment thereof according to claim 2, wherein the posttranslational modification is pyroglutamylation at the N terminal of the heavy chain variable region and/or deletion of lysine at the C terminal of the heavy chain.

5. The anti-human Fn14 antibody or the antigen-binding fragment thereof according to claim 2, comprising:
a heavy chain variable region consisting of the amino acid sequence of amino acid numbers 1 to 125 of SEQ ID NO: 2, in which glutamine of amino acid number 1 of SEQ ID NO: 2 is modified to pyroglutamic acid; and
a light chain variable region consisting of the amino acid sequence of amino acid numbers 1 to 114 of SEQ ID NO: 4.

6. The anti-human Fn14 antibody according to claim 2, selected from:
an anti-human Fn14 antibody comprising a heavy chain consisting of the amino acid sequence represented by SEQ ID NO: 2 and a light chain consisting of the amino acid sequence represented by SEQ ID NO: 4; and
an anti-human Fn14 antibody comprising a heavy chain consisting of the amino acid sequence represented by SEQ ID NO: 2 and a light chain consisting of the amino acid sequence represented by SEQ ID NO: 4, wherein the antibody comprises a posttranslational modification.

7. The anti-human Fn14 antibody according to claim 6, comprising:
a heavy chain consisting of the amino acid sequence represented by SEQ ID NO: 2; and
a light chain consisting of the amino acid sequence represented by SEQ ID NO: 4.

8. The anti-human Fn14 antibody according to claim 6, wherein the posttranslational modification is pyroglutamylation at the N terminal of the heavy chain and/or deletion of lysine at the C terminal of the heavy chain.

9. The anti-human Fn14 antibody according to claim 8, comprising:
a heavy chain consisting of the amino acid sequence of amino acid numbers 1 to 454 of SEQ ID NO: 2, in which glutamine of amino acid number 1 of SEQ ID NO: 2 is modified to pyroglutamic acid; and
a light chain consisting of the amino acid sequence represented by SEQ ID NO: 4.

10. The antigen-binding fragment according to claim 1, which is a single chain variable region fragment, Fab, Fab', or F(ab')$_2$.

11. A polynucleotide comprising:
a base sequence encoding the heavy chain variable region of the anti-human Fn14 antibody or the antigen-binding fragment thereof according to claim 3.

12. A polynucleotide comprising:
a base sequence encoding the light chain variable region of the anti-human Fn14 antibody or the antigen-binding fragment thereof according to claim 3.

13. An expression vector comprising:
a polynucleotide encoding the heavy chain variable region and/or the light chain variable region of the anti-human Fn14 antibody or the antigen-binding fragment thereof according to claim 3.

14. A host cell selected from the group consisting of the following (a) to (d):
- (a) a host cell transformed with an expression vector comprising a polynucleotide comprising a base sequence encoding the heavy chain variable region of the anti-human Fn14 antibody or the antigen-binding fragment thereof according to claim 3 and a polynucleotide comprising a base sequence encoding the light chain variable region of the antibody or the antigen-binding fragment thereof according to claim 3;
- (b) a host cell transformed with an expression vector comprising a polynucleotide comprising a base sequence encoding the heavy chain variable region of the anti-human Fn14 antibody or the antigen-binding fragment thereof according to claim 3, and an expression vector comprising a polynucleotide comprising a base sequence encoding the light chain variable region of the antibody or the antigen-binding fragment thereof according to claim 3;
- (c) a host cell transformed with an expression vector comprising a polynucleotide comprising a base sequence encoding the heavy chain variable region of the anti-human Fn14 antibody or the antigen-binding fragment thereof according to claim 3; and
- (d) a host cell transformed with an expression vector comprising a polynucleotide comprising a base sequence encoding the light chain variable region of the anti-human Fn14 antibody or the antigen-binding fragment thereof according to claim 3.

15. A host cell selected from the group consisting of the following (e) to (h):
- (e) a host cell transformed with an expression vector comprising a polynucleotide comprising a base sequence encoding the heavy chain of the anti-human Fn14 antibody according to claim 7 and a polynucleotide comprising a base sequence encoding the light chain of the antibody according to claim 7;
- (f) a host cell transformed with an expression vector comprising a polynucleotide comprising a base sequence encoding the heavy chain of the anti-human Fn14 antibody according to claim 7, and an expression vector comprising a polynucleotide comprising a base sequence encoding the light chain of the antibody according to claim 7;
- (g) a host cell transformed with an expression vector comprising a polynucleotide comprising a base sequence encoding the heavy chain of the anti-human Fn14 antibody according to claim 7; and
- (h) a host cell transformed with an expression vector comprising a polynucleotide comprising a base sequence encoding the light chain of the anti-human Fn14 antibody according to claim 7.

16. A method for producing an anti-human Fn14 antibody or an antigen-binding fragment thereof, the method comprising:
culturing a host cell selected from the group consisting of the following (A) to (C) to express an anti-human Fn14 antibody or an antigen-binding fragment thereof:
- (A) a host cell transformed with an expression vector comprising a polynucleotide comprising a base sequence encoding the heavy chain variable region of the anti-human Fn14 antibody or the antigen-binding fragment thereof according to claim 3 and a polynucleotide comprising a base sequence encoding the light chain variable region of the antibody or the antigen-binding fragment thereof according to claim 3;
- (B) a host cell transformed with an expression vector comprising a polynucleotide comprising a base sequence encoding the heavy chain variable region of the anti-human Fn14 antibody or the antigen-binding fragment thereof according to claim 3, and an expression vector comprising a polynucleotide comprising a base sequence encoding the light chain variable region of the antibody or the antigen-binding fragment thereof according to claim 3; and
- (C) a host cell transformed with an expression vector comprising a polynucleotide comprising a base sequence encoding the heavy chain variable region of the anti-human Fn14 antibody or the antigen-binding fragment thereof according to claim 3, and a host cell transformed with an expression vector comprising a polynucleotide comprising a base sequence encoding the light chain variable region of the antibody or the antigen-binding fragment thereof according to claim 3.

17. A method for producing an anti-human Fn14 antibody comprising:
culturing a host cell selected from the group consisting of the following (D) to (F) to express an anti-human Fn14 antibody:
- (D) a host cell transformed with an expression vector comprising a polynucleotide comprising a base sequence encoding the heavy chain of the anti-human Fn14 antibody according to claim 7 and a polynucleotide comprising a base sequence encoding the light chain of the antibody according to claim 7;
- (E) a host cell transformed with an expression vector comprising a polynucleotide comprising a base sequence encoding the heavy chain of the anti-human Fn14 antibody according to claim 7, and an expression vector comprising a polynucleotide comprising a base sequence encoding the light chain of the antibody according to claim 7; and
- (F) a host cell transformed with an expression vector comprising a polynucleotide comprising a base sequence encoding the heavy chain of the anti-human Fn14 antibody according to claim 7, and a host cell transformed with an expression vector comprising a polynucleotide comprising a base sequence encoding the light chain of the anti-human Fn14 antibody according to claim 7.

18. An anti-human Fn14 antibody or an antigen-binding fragment thereof produced by the method according to claim 16.

19. An anti-human Fn14 antibody produced by the method according to claim 17.

20. A pharmaceutical composition comprising:
the anti-human Fn14 antibody or the antigen-binding fragment thereof according to claim 1; and
a pharmaceutically acceptable excipient.

21. A pharmaceutical composition comprising:
the anti-human Fn14 antibody or the antigen-binding fragment thereof according to claim 3, wherein, optionally, the glutamine of amino acid number 1 of SEQ ID NO: 2 is modified to pyroglutamic acid; and
a pharmaceutically acceptable excipient.

22. A pharmaceutical composition comprising:
the anti-human Fn14 antibody according to claim 7, wherein, optionally, the glutamine of amino acid number 1 of SEQ ID NO: 2 is modified to pyroglutamic acid; and
a pharmaceutically acceptable excipient.

23. A method for treating colon cancer cachexia, the method comprising:
    administering a therapeutically effective amount of the anti-human Fn14 antibody or the antigen-binding fragment thereof according to claim 1.

24. A method of treating colon cancer or colon cancer cachexia, comprising:
    administering to a subject with colon cancer of colon cancer cachexia a pharmaceutical composition comprising the anti-human Fn14 antibody or the antigen-binding fragment thereof according to claim 1 as an active ingredient,
    wherein the pharmaceutical composition is used in combination with an anticancer agent.

25. A method of treating colon cancer or colon cancer cachexia, comprising:
    administering to a subject with colon cancer of colon cancer cachexia a pharmaceutical composition comprising an anticancer agent,
    wherein the pharmaceutical composition is used in combination with the anti-human Fn14 antibody or the antigen-binding fragment thereof according claim 1.

\* \* \* \* \*